US011200664B2

(12) United States Patent
Yuh et al.

(10) Patent No.: US 11,200,664 B2
(45) Date of Patent: Dec. 14, 2021

(54) INTERPRETATION AND QUANTIFICATION OF EMERGENCY FEATURES ON HEAD COMPUTED TOMOGRAPHY

(71) Applicant: The Regents of the University of California, Oakland, CA (US)

(72) Inventors: Esther L. Yuh, San Francisco, CA (US); Pratik Mukherjee, San Francisco, CA (US); Geoffrey T. Manley, Lafayette, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/782,005

(22) PCT Filed: Dec. 16, 2016

(86) PCT No.: PCT/US2016/067170
§ 371 (c)(1),
(2) Date: Jun. 6, 2018

(87) PCT Pub. No.: WO2017/106645
PCT Pub. Date: Jun. 22, 2017

(65) Prior Publication Data
US 2018/0365824 A1 Dec. 20, 2018

Related U.S. Application Data

(60) Provisional application No. 62/269,778, filed on Dec. 18, 2015.

(51) Int. Cl.
*G06K 9/00* (2006.01)
*G06T 7/00* (2017.01)
(Continued)

(52) U.S. Cl.
CPC ............ *G06T 7/0012* (2013.01); *A61B 6/032* (2013.01); *A61B 6/501* (2013.01); *G06K 9/4628* (2013.01);
(Continued)

(58) Field of Classification Search
CPC ......... G06T 7/0012; G06T 7/136; G06T 7/62; G06T 7/68; G06T 7/11; G06T 6/032;
(Continued)

(56) References Cited

U.S. PATENT DOCUMENTS 6,351,573 B1 * 2/2002 Schneider ............. G06F 19/321
382/128
6,775,404 B1 * 8/2004 Pagoulatos ............... G06T 3/00
128/916

(Continued)

FOREIGN PATENT DOCUMENTS

JP 2013-198763 3/2013
WO 03060827 7/2003

OTHER PUBLICATIONS

Plassard et al. (2015) "Revealing latent value of clinically acquired CTs of traumatic brain injury through multi-atlas segmentation in a retrospective study of 1,003 with external cross-validation" Medical Imaging 2015: Image Processing, vol. 9413, International Society for Optics and Photonics, pp. 1-13.
(Continued)

*Primary Examiner* — Marceau Milord
(74) *Attorney, Agent, or Firm* — Edward J. Baba; Peter W. Schroen; Bozicevic, Field & Francis LLP

(57) ABSTRACT

A computer-based method for quantitative evaluation of computed tomography (CT) images of the head, particularly in circumstances of neurological emergency such as acute intracranial hemorrhage, evidence of intracranial mass effect, and acute stroke. The method comprises: calculation
(Continued)

Localization of Basilar Cistern Pixels and Assessment of its Morphology and Volume for Evidence of Downward Cerebral Herniation of volumes of abnormal areas such as locations of hemorrhage; quantification of severity of midline shift and basilar cistern effacement; and rapid identification of anatomical locations of abnormal findings. The methods comprise use of heuristics, convolutional neural networks, deep learning, edge detection, and Hough transform.

28 Claims, 17 Drawing Sheets

(51) Int. Cl.
*A61B 6/03* (2006.01)
*A61B 6/00* (2006.01)
*G06K 9/46* (2006.01)
*G06T 7/68* (2017.01)
*G06K 9/62* (2006.01)
*G06T 7/62* (2017.01)
*G06T 7/136* (2017.01)
*G06T 7/11* (2017.01)

(52) U.S. Cl.
CPC .......... *G06K 9/628* (2013.01); *G06K 9/6262* (2013.01); *G06K 9/6272* (2013.01); *G06T 7/11* (2017.01); *G06T 7/136* (2017.01); *G06T 7/62* (2017.01); *G06T 7/68* (2017.01); *G06K 2209/05* (2013.01); *G06K 2209/051* (2013.01); *G06T 2207/10081* (2013.01); *G06T 2207/20061* (2013.01); *G06T 2207/20072* (2013.01); *G06T 2207/20081* (2013.01); *G06T 2207/20084* (2013.01); *G06T 2207/30016* (2013.01)

(58) Field of Classification Search
CPC . G06T 2207/20072; G06T 2207/20081; G06T 2207/20084; G06T 2207/30016; A61B 6/032; A61B 6/501; G06K 9/4628; G06K 9/6272; G06K 9/628; G06K 2209/05; G06K 2209/051
USPC ........................................................ 382/131
See application file for complete search history.

(56) References Cited

U.S. PATENT DOCUMENTS

| | | | | |
|---|---|---|---|---|
| 7,286,694 | B2* | 10/2007 | Oosawa | G06T 7/0012 378/20 |
| 7,903,849 | B2* | 3/2011 | Kimura | G06T 7/30 382/128 |
| 8,374,414 | B2* | 2/2013 | Tang | G06K 9/4604 382/131 |
| 8,798,343 | B2* | 8/2014 | Kabus | G06T 7/33 382/128 |
| 9,165,360 | B1 | 10/2015 | Bates et al. | |
| 9,962,086 | B2* | 5/2018 | Dabbah | G16H 50/30 |
| 10,117,597 | B2* | 11/2018 | Beckers | A61B 5/0263 |
| 10,282,663 | B2* | 5/2019 | Socher | G06F 17/50 |
| 10,360,999 | B2* | 7/2019 | Bernard | A61B 5/002 |
| 10,438,345 | B2* | 10/2019 | Wenzel | G06T 7/0012 |
| 2003/0071739 | A1* | 4/2003 | Addy | G08B 13/08 340/686.1 |
| 2003/0099388 | A1* | 5/2003 | Doi | G06T 5/50 382/131 |
| 2005/0148859 | A1* | 7/2005 | Miga | G06K 9/00214 600/410 |
| 2006/0074290 | A1* | 4/2006 | Chen | G06T 7/0012 600/407 |
| 2006/0152618 | A1* | 7/2006 | Yamasaki | G03B 17/48 348/345 |
| 2008/0021502 | A1* | 1/2008 | Imielinska | A61B 6/032 607/1 |
| 2010/0145194 | A1 | 6/2010 | Joshi et al. | |
| 2012/0114205 | A1* | 5/2012 | Tang | G06K 9/4642 382/131 |
| 2012/0184840 | A1* | 7/2012 | Najarian | G06T 7/0012 600/408 |
| 2013/0223714 | A1* | 8/2013 | Lipton | G06T 7/0012 382/131 |
| 2013/0303900 | A1* | 11/2013 | Nowinski | A61B 5/7275 600/425 |
| 2014/0328517 | A1* | 11/2014 | Gluncic | G06K 9/00 382/103 |
| 2015/0080703 | A1* | 3/2015 | Reiman | A61B 5/4848 600/409 |
| 2015/0324690 | A1 | 11/2015 | Chilimbi et al. | |
| 2016/0015471 | A1* | 1/2016 | Piron | A61B 34/10 600/424 |
| 2016/0019693 | A1* | 1/2016 | Silbersweig | G06T 7/0012 382/128 |
| 2016/0035093 | A1* | 2/2016 | Kateb | A61B 5/0042 382/131 |
| 2016/0070436 | A1* | 3/2016 | Thomas | A61B 5/055 715/771 |
| 2016/0143574 | A1* | 5/2016 | Jones | A61B 5/4076 600/544 |
| 2016/0239969 | A1* | 8/2016 | Davatzikos | G06T 7/0014 |
| 2016/0292864 | A1* | 10/2016 | Dabbah | A61B 6/486 |
| 2017/0046616 | A1* | 2/2017 | Socher | G06K 9/4628 |
| 2017/0132491 | A1* | 5/2017 | Feiweier | A61B 5/0042 |
| 2017/0236294 | A1* | 8/2017 | Fisher | A61B 5/0263 600/419 |
| 2017/0315036 | A1* | 11/2017 | Xuan | G01N 3/18 |
| 2018/0338835 | A1* | 11/2018 | Gordon | A61F 2/2875 |
| 2019/0012783 | A1* | 1/2019 | Zahid | A61B 6/032 |
| 2019/0038167 | A1* | 2/2019 | Jones | A61B 5/0478 |
| 2019/0053744 | A1* | 2/2019 | Janigro | A61B 5/150022 |
| 2019/0213482 | A1* | 7/2019 | Socher | G06F 17/50 |

OTHER PUBLICATIONS

Suzuki (2011) "Pixel-Based Machine Learning in Medical Imaging" International Journal of Biomedical Imaging, vol. 2012, pp. 1-18.

Bhavna et al. (2014) "Classification of hematomas in brain CT images using neural network", 2014 International Conference on Issues and Challenges in Intelligent Computing Techniques (ICICT), IEEE, pp. 41-46.

Hariharan et al. (2014) "Simultaneous Detection and Segmentation" In: "Serious Games", Springer International publishing, vol. 8695, pp. 297-312.

Long et al. (2015) "Fully convolutional networks for semantic segmentation", IEEE Conference on Computer Vision and Pattern Recognition, vol. 39, No. 4, pp. 3431-3440.

Ren et al. (2015) "Faster R-CNN: Towards Real-Time Object Detection with Region Proposal Networks", Advances In neural Information Processing Systems.

Yuh et al. (2008) "Computer-Aided Assessment of Head Computed Tomography (CT) Studies in Patients with Suspected Traumatic brain Injury", Journal of Neurotrauma, vol. 25, No. 10, pp. 1163-1172.

Sezgin et al. (2004) "Survey over image thresholding techniques and quantitative performance evaluation" Journal of Electronic Imaging 13(1), pp. 146-165.

He et al. (2015) "Deep Residual Learning for Image Recognition", arXiv, pp. 1-12.

Yu et al. (2015) "Multi-scale context aggregation with dilated convolutions", pp. 1-9.

\* cited by examiner

FIG. 8
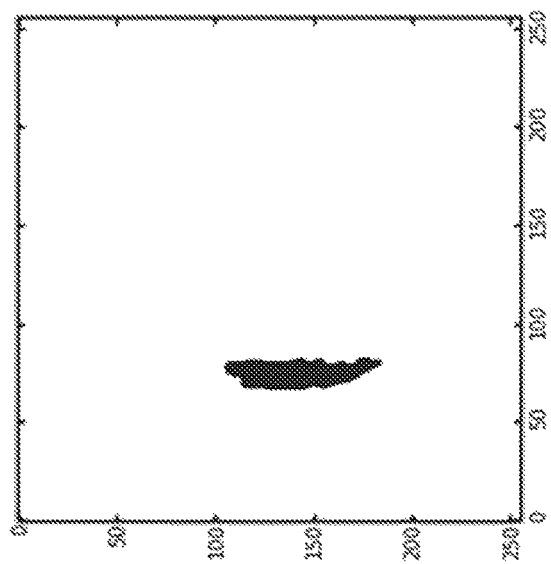
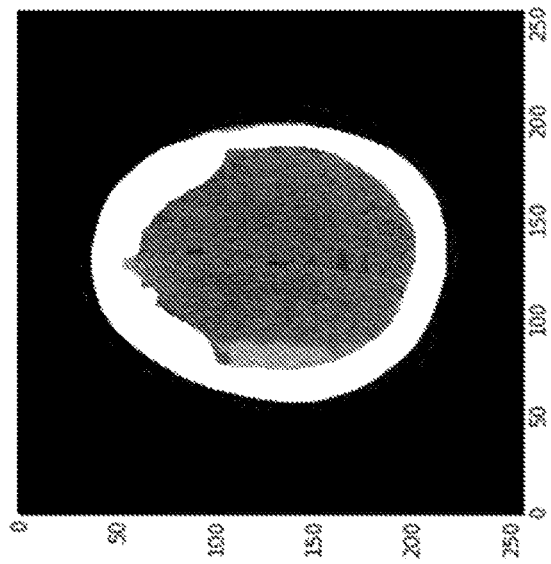
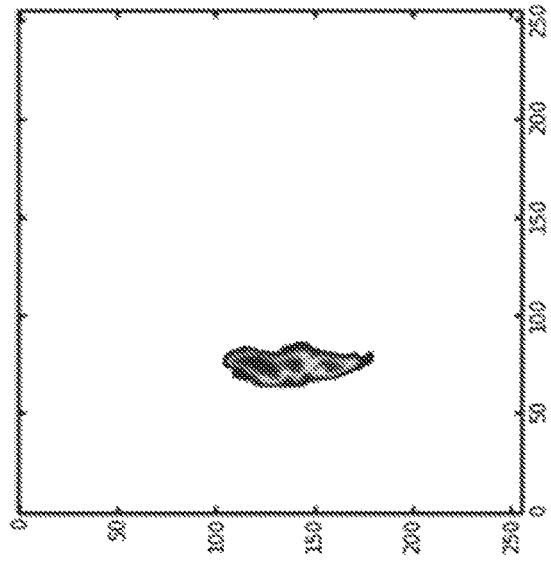

Streak artifact due to metal in right orbit

Localization of Basilar Cistern Pixels and Assessment of its Morphology and Volume for Evidence of Downward Cerebral Herniation Localization of Ventricular Pixels and Assessment of Morphology and Volume for Evidence of Midline Shift Lateral ventricle bodies
Area = 9 cm²
High symmetry
Centroid within 3 mm of midline

INTERPRETATION AND QUANTIFICATION OF EMERGENCY FEATURES ON HEAD COMPUTED TOMOGRAPHY

CROSS REFERENCE TO RELATED APPLICATIONS

This application claims the benefit of U.S. Provisional Application No. 62/269,778, filed Dec. 18, 2015, which application is incorporated herein by reference in its entirety.

TECHNICAL FIELD

The technology described herein relates to quantitative evaluation of head computed tomography (CT) images, and in particular to computer algorithmic methods and computer hardware implementations for carrying out the same.

BACKGROUND

It has long been recognized that in the rapid initial assessment of patients with suspected head trauma, acute hemorrhagic or ischemic stroke, or other neurological emergencies, head computed tomography (CT) scans play a critical role in determining subsequent steps in treatment, including, for example, whether the patient needs hospitalization, early surgical treatment, and/or the administration of medications such as thrombolytic agents for ischemic stroke (as well as absence of contraindications to the same).

Accordingly, there is a need for a method of rapid interpretation of such CT studies that would significantly expedite triage to hospitalization, neurosurgical consultation, immediate surgical intervention, or administration of medications. This is especially important as CT is increasingly becoming a portable, point-of-care imaging technology that is available in ambulances, intensive care units, hospital wards, surgical suites, and on the battlefield. In addition, quantitative analyses of CT scans and extraction of quantitative parameters that is not possible by the unaided human eye would be useful for improved prognostication, better-informed decisions about the need for surgical management and other specialized care, and more standardized practice guidelines based on quantitative data rather than subjective impressions. Such quantitative data includes, e.g., calculation of volumes of abnormal areas including areas of hemorrhage, and quantification of severity of midline shift and basilar cistern effacement. Both qualitative and quantitative data would be immediately useful to clinical staff, and could be swiftly incorporated into radiological reports and other medical records.

To date, heuristic algorithms have been proposed for head CT analysis, but they have generally fallen short of the accuracy levels needed to achieve real clinical utility, due in part to the high variability in appearance of abnormalities.

The discussion of the background herein is included to explain the context of the technology. This is not to be taken as an admission that any of the material referred to was published, known, or part of the common general knowledge as at the priority date of any of the claims found appended hereto.

Throughout the description and claims of the instant application the word "comprise" and variations thereof, such as "comprising" and "comprises", is not intended to exclude other additives, components, integers or steps.

SUMMARY

The instant disclosure addresses computer-implemented methods for the processing of head computed tomography (CT) scans for neurological emergencies, including acute intracranial hemorrhage, evidence of intracranial mass effect, and acute stroke including hemorrhagic and ischemic stroke. In addition to providing rapid computer-aided diagnostic information from head CT exams, the disclosure includes methods for performing quantitative analyses of CT scans, including extraction of quantitative parameters and other information that cannot be obtained by visual interpretation alone. Such analyses include calculation of volumes of abnormal areas including, but not limited to, areas of hemorrhage, quantification of severity of midline shift and basilar cistern effacement, and rapid identification of anatomical locations of these abnormal findings. The methods can be implemented on image-processing workstations, installed directly on CT scanner console computers, or on remote servers for central "cloud"-based processing of CT scans via computer networks.

The present disclosure includes both heuristic algorithms that have been custom designed for head CT analysis, and a type of convolutional neural network (CNN) trained to identify abnormal features using dense pixelwise labeling from manually segmented head CT images as well as another type of convolutional neural network trained to identify abnormal features from boxes that are manually drawn around those features.

Detection of different types of abnormal features on head CT scans is addressed here in modular fashion, with different approaches used to evaluate different aspects of the head CT. The different algorithms combine heuristic and neural network approaches.

A particular embodiment of a system for detection of abnormal CT features may include all of the approaches described herein, or may include a subset such as one, two or more of the steps. Furthermore, because of the modular nature of the architecture of the head CT interpretation system described herein, the algorithms and approaches it comprises may be executed in the same or in a different order than described herein, without significantly differing from the purpose or manner of operation.

BRIEF DESCRIPTION OF THE DRAWINGS

FIG. 7B: Head CT image; FIG. 7C: radiologist's manual demarcation of abnormality);

FIG. 8 shows an example application of a system described herein for detection of a subdural hemorrhage such as in traumatic intracranial hemorrhage (FIG. 8A:

Automated demarcation of abnormality; FIG. 8B: Head CT image; FIG. 8C: radiologist's manual demarcation of abnormality);

FIG. 9B: Head CT image; FIG. 9C: radiologist's manual demarcation of abnormality);

DETAILED DESCRIPTION

Aspects of Computer System Implementations

Figure 1:
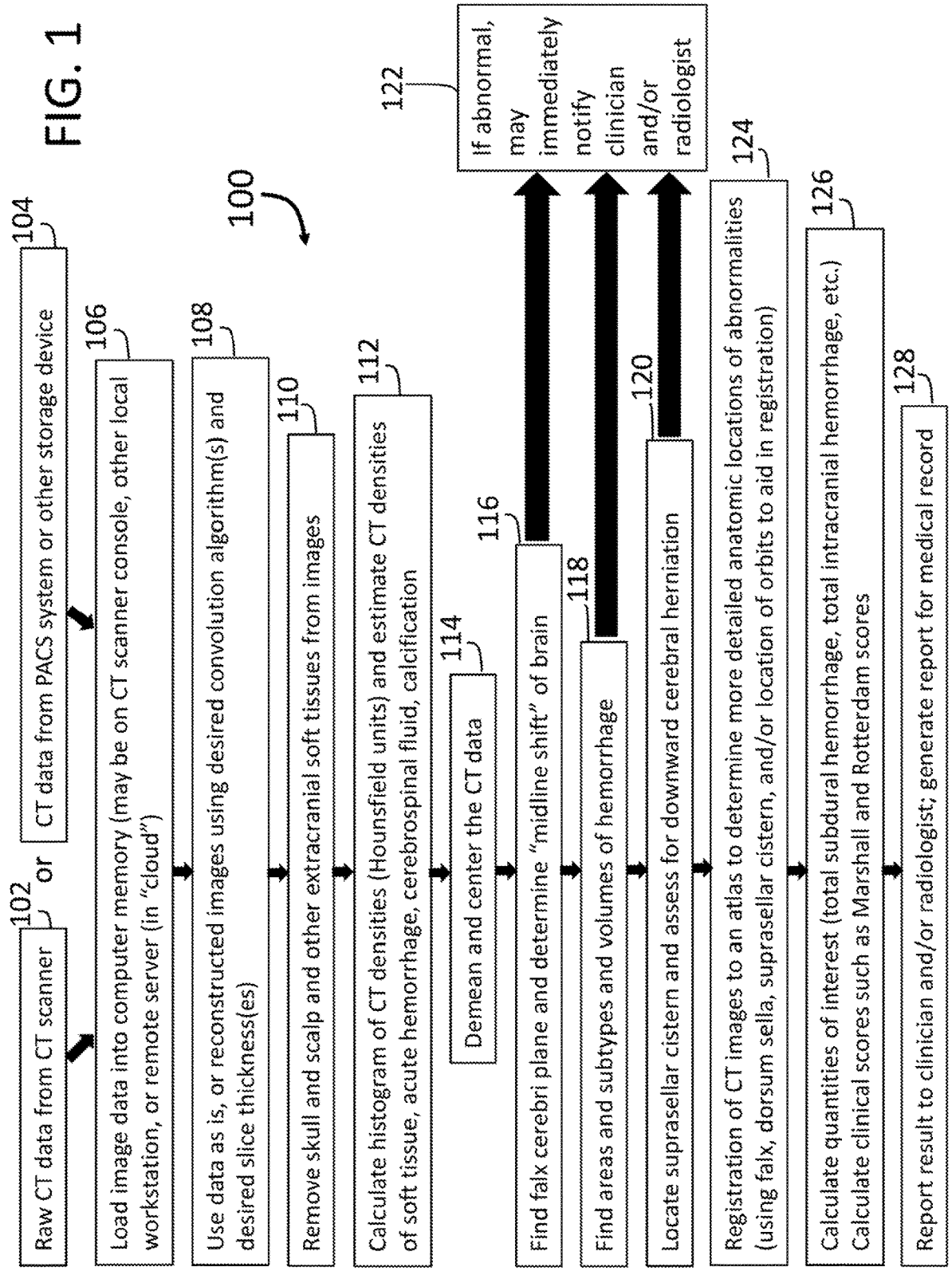
FIG. 1 shows a flow-chart of a method for automated interpretation and quantification of emergency features on head computed tomography.

FIG. 1 shows a block diagram of a method 100 for detection of abnormal features on head CT images. The process begins at 102 or at 104, where head CT data are generated on a CT scanner, or identified on some other local or remote computer storage device such as PACS (Picture Archiving and Communication System).

Figure 2:
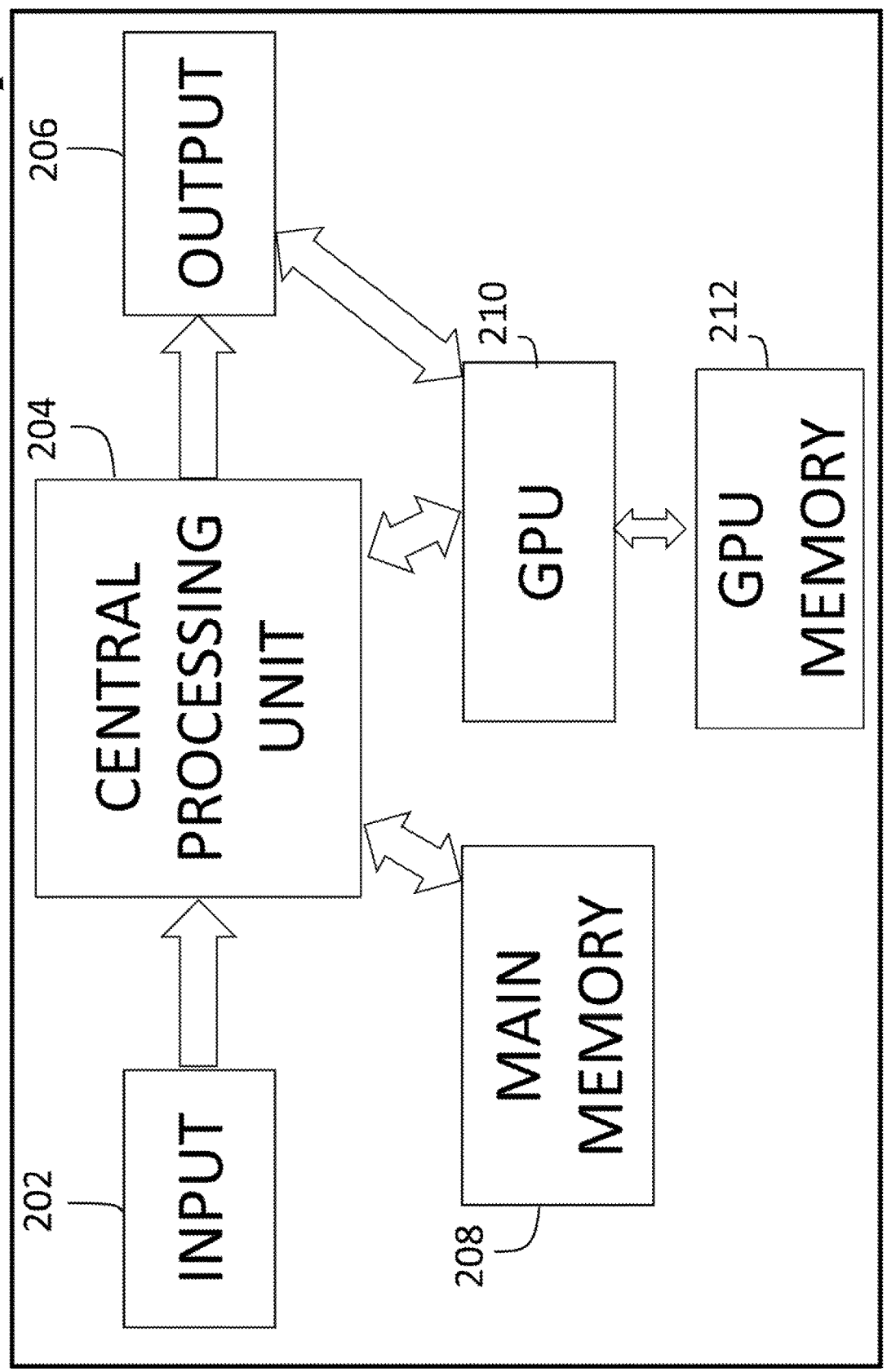
FIG. 2 shows a schematic of an apparatus for an exemplary computer system used in multiple steps of FIG. 1.

In 106, these CT data are loaded into the memory of a computer system, an example of whose general architecture is shown in FIG. 2.

Turning briefly to FIG. 2, a computer system in FIG. 2 that can be configured to perform various of the subsequent steps in FIG. 1 for analysis of the CT images can be located within the CT scanner console itself, or can be another workstation, or can be a remote server in the "cloud" accessible via computer network. As shown in FIG. 2, this computer system may generally include at least one input (such as a user interface) 202, at least one processor (such as a central processing unit) 204, at least one type of memory 206 which will typically include both high speed random access memory as well as non-volatile memory (such as one or more magnetic disk drives), at least one output 208 (such as a monitor or other display device), a disk (not shown) for storage of image and other data (not shown), and a device or devices for reading computer media. The computer system may preferably comprise a GPU (graphics processing unit) 210 in conjunction with GPU memory 212, as further described herein. The computer system 200 may be, for example, a workstation, network server, laptop, tablet, or notebook computer, personal digital assistant, smartphone, or mainframe computer. Additionally, and not shown in FIG. 2, the computer system may have at least one network connection or other communication interface for communicating with other computers over a network, including the Internet, as well as other devices, such as via a high speed networking cable, or a wireless connection. The network connection can be used for a hospital to share data (such as CT data and results of analysis with the methods herein) with another party, where the other party has a second computer system (not shown) having similar capability to that of computer system 200, and is able to receive data to be shared from computer 200. There may optionally be a firewall (not shown) between computer 200 and a network such as the Internet. At least one or more processors 204, memory 208, and user interface or input 202, communicate with one another via at least one communication bus (not shown).

Memory 208 stores procedures and data, typically including some or all of: an operating system for providing basic system services; one or more application programs, such as a parser, and a compiler, a file system, one or more databases that store image and other medical data, and optionally a floating point coprocessor where necessary for carrying out high level mathematical operations such as for carrying out image analysis. The methods of the present technology may also draw upon functions contained in one or more dynamically linked libraries stored either in memory 208, or on disk.

The data and other routines that are stored in memory may instead, optionally, be stored on a disk where the amount of data in the database is too great to be efficiently stored in memory 208. The data and routines may also instead, or in part, be stored on one or more remote computers that communicate with computer system 200 through network interface, according to networking methods understood by those skilled in the art.

In particular, memory 208 is encoded with instructions for at least: carrying out image analysis of CT image data. The instructions can further include programmed instructions for performing one or more of analysis via convolutional neural networks, deep learning analysis, and heuristic techniques as desired.

Various implementations of the technology herein can be contemplated, particularly as performed on one or more computing apparatuses (machines that can be programmed to perform arithmetic) of varying complexity, including, without limitation, workstations, PC's, laptops, notebooks, tablets, netbooks, and other mobile computing devices, including cell-phones, mobile phones, wearable devices, and personal digital assistants. The methods herein may further be susceptible to performance on quantum computers. The computing devices can have suitably configured processors, including, without limitation, graphics processors and math coprocessors, for running software that carries out the methods herein. In addition, certain computing functions are typically distributed across more than one computer so that, for example, one computer accepts input and instructions, and a second or additional computers receive the instructions via a network connection and carry out the processing at a remote location, and optionally communicate results or output back to the first computer.

Control of the computing apparatuses can be via a user interface 202, which may comprise one or more of: a display, mouse, keyboard, and/or other items not shown in FIG. 2, such as a track-pad, track-ball, touch-screen, stylus, speech-recognition device, gesture-recognition technology, human fingerprint reader, or other input such as based on a user's eye-movement, or any subcombination or combination of inputs thereof.

In one embodiment, the computing apparatus can be configured to restrict user access, such as by scanning a QR-code, use of gesture recognition, biometric data input, a fingerprint reader, voice recognition, or password input.

The manner of operation of the technology, when reduced to an embodiment as one or more software modules, functions, or subroutines, can be in a batch-mode—as on a stored database of CT data, processed in batches, or by interaction with a user who inputs specific instructions for a single image or related collection of images.

The image analyses created by the technology herein, as well as the images themselves, can be displayed in tangible form, such as on one or more computer displays, such as a monitor, laptop display, or the screen of a tablet, notebook, netbook, or cellular phone or wearable device. The image analyses can further be printed to paper form, stored as electronic files in a format for saving on a computer-readable medium or for transferring or sharing between computers, or projected onto a screen of an auditorium such as during a presentation.

Certain default settings can be built in to a computer-implementation, but the user can be given as much choice as he or she desires over the features that are used in analyzing the CT data.

CT Image Pre-Processing

CT images are generally provided as a stack of 2D slices through which a radiologist scrolls in one direction or another. The 2D slices can be displayed as sections of arbitrary thickness. They can also be displayed after doing some basic image processing that facilitates review, such as to highlight bony detail, or to make soft tissue stand out better. The stack can be displayed in an arbitrary choice of 2D plane or as a 3D rendering. The present technology can be applied regardless of any particular choice of parameters such as slice thickness or type of reconstruction.

Returning now to the flowchart in FIG. 1, at 108, the CT data may (but do not necessarily need to) be altered by reconstructing them into images using specific reconstruction kernels, e.g., "soft tissue algorithm" or "bone algorithm." Note that "reconstruction kernel" here is a term used in CT image reconstruction that specifically refers to application of local filters to the CT data that result in different appearances of the images for human viewing, for example, to make bony detail stand out better, or to make soft tissue stand out better. The images can also be reconstructed in various planes such as coronal, sagittal or axial, or as determined by alignment with a specific anatomic structure or structures or anatomic template. The images can also be reconstructed at different "slice thicknesses", often 2.5 or 5 mm for clinical images, though thinner slice reconstructions of as little as 0.5 or 0.625 mm are possible for CT data obtained on many modern multirow-detector CT scanners.

At 110, all or most of the skull and scalp and other extracranial soft tissues, such as in the patient's face, are removed from the images using heuristic algorithms. Although the whole head (including skull, scalp and/or other extracranial soft tissues) could be used to train the convolutional neural network (CNN) even when the purpose is to assess for intracranial abnormalities, the training may proceed more quickly and with less training data and/or shallower or less complex CNNs if all or most of the skull, face and other extracranial soft tissues are removed first through heuristic methods.

The step 110 can be performed by any of several methods, for example, including, but not limited to: thresholding at a high Hounsfield unit number to identify most of the skull and facial bones; next performing a close operation, followed by an open operation, on the resulting bone to close off all skull base foramina, burr holes, or other discontinuities in the skull, and thereby achieving a continuous high-density "vault" that completely encloses the brain; and finally performing a fill operation and subtracting the images prior to and following the fill operation, in order to isolate the intracranial space.

Skull and facial removal at 110 can be aided using dual-energy and spectral CT techniques, whereby calcifications and other high-density materials that mimic acute hemorrhage are identified through their dual-energy or spectral CT characteristics. Parts of the skull and facial bones can be identified through these techniques and used to support heuristic algorithms to remove the skull and face as described herein. Dual-energy and spectral CT can also be used as an additional step to remove stray calcifications such as vascular and dural calcifications that may remain after the skull, skull base, and facial bones have been mostly removed through the heuristic techniques. Although this latter step is not essential, it may enhance the performance of CNN algorithms proposed here for identification of intracranial hemorrhage, since many of the false-positive intracranial hemorrhages that may be identified by CNNs (as well as heuristic algorithms) consist of areas of high CT attenuation (Hounsfield Units, or H.U.) that are within the typical H.U. range of acute hemorrhage; such areas include, for example, calcifications.

In 112, the histogram of CT densities (e.g., in Hounsfield units) is calculated for each slice or for the entire stack of CT images. By fitting this histogram to a sum of, for example, Gaussian distributions centered at the expected approximate locations of CT densities for soft tissue, acute hemorrhage, cerebrospinal fluid, and calcification, the CT densities for these different tissues and fluids is determined for the particular CT images at hand. This step is not essential, but can improve performance of some of the heuristic algorithms described herein, when small deviations of the apparent Hounsfield units from their true values occur due to technical issues, such as CT scanners that are slightly out of calibration.

In 114, the CT data are demeaned and normalized such that their average is 0 and their standard deviation is 1. This step is not essential but may be helpful for improving the performance of the convolutional neural networks.

Detection of Cerebral Midline Shift

Cerebral midline shift, also sometimes referred to as subfalcine herniation, is a distinct abnormality from intracranial hemorrhage but evaluation of it is an essential part of interpreting a head CT scan. Cerebral midline shift can be an emergency feature on head CT. In 116, this important feature is identified and is quantified by the degree of shift of the cerebral ventricular system relative to the falx cerebri, as described elsewhere herein.

Figure 3:
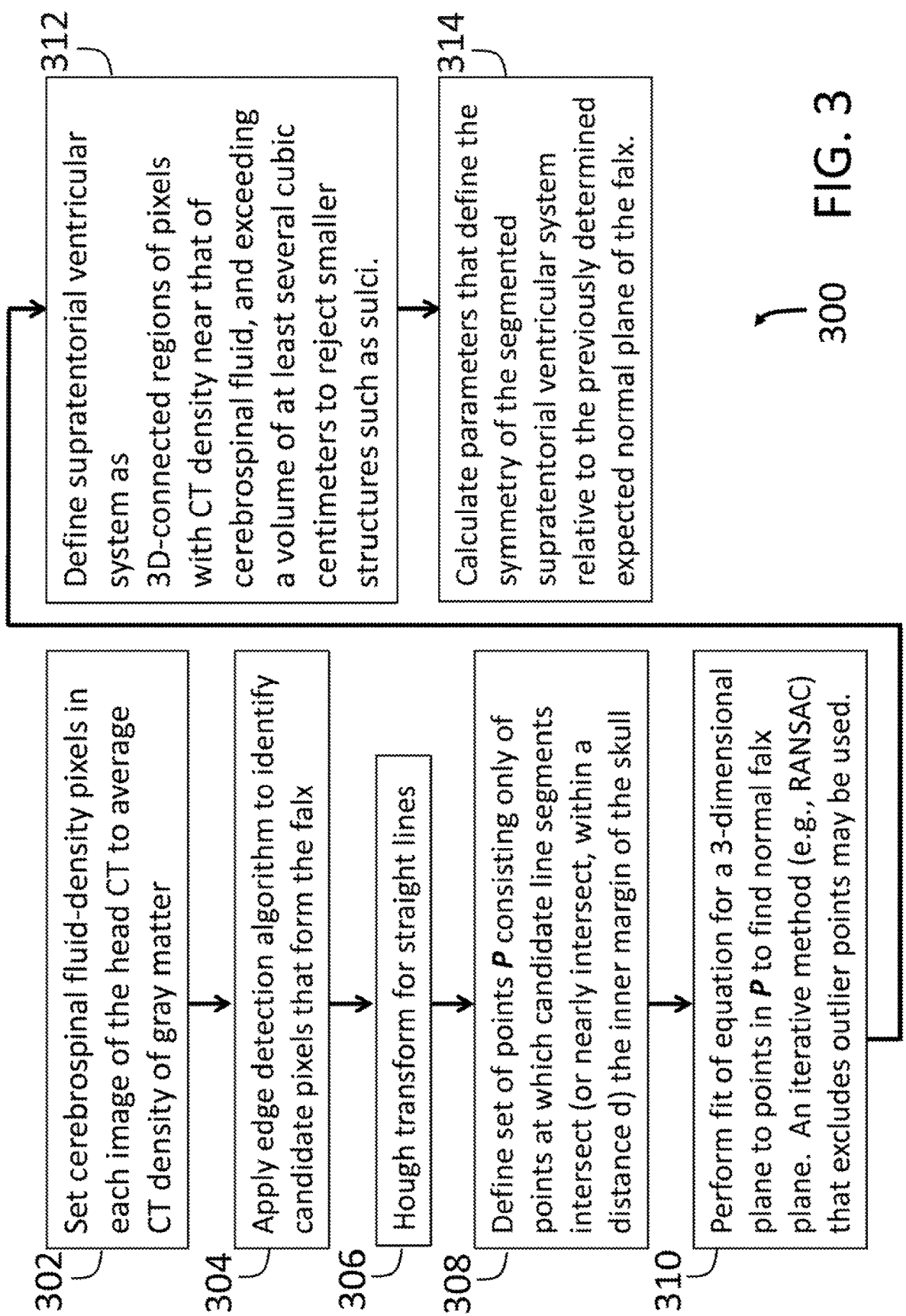
FIG. 3 shows a heuristic method for quantitative characterization of cerebral midline shift.

We turn briefly to FIG. 3, which shows how a heuristic algorithm can be used to determine the midline shift. Specifically, FIG. 3 shows an example of one heuristic method for achieving the function described in 116 with good accuracy.

Although CT images are typically acquired with the head in a standard orientation, this sometimes cannot be achieved particularly for disoriented, confused or unconscious patients. Prior to locating the falx cerebri, it can be helpful to first identify gross rotation or tilt of the head and correct for it in order to improve registration results. One heuristic method for determining an initial estimate of the head pose is to localize certain characteristic anatomic features or landmarks, such as facial features that are generally reliable and rarely altered, even in the presence of brain distortion in head trauma. In one embodiment, a specific facial feature, the globes, colloquially known as "eyeballs", are identified by application of a circular Hough transform. The positions of the centerpoints of the globes then define gross head tilt or rotation, and thereby allow approximate correction of the orientation of the head, aiding in subsequent registration to an atlas, as well as allowing identification of the midline of the intracranial space where midline structures, such as the falx cerebri and the basilar cistern, are expected to be approximately located.

An anatomic structure known as the falx cerebri is a very important structure because it defines the location of the normal midline plane that separates the left and right cerebral hemispheres. Radiologists look for cerebral midline shift by assessing whether the brain is shifted to the right of this line or to the left of this line. In one embodiment shown in 302, 304, and 306 of FIG. 3, the falx is located by application of an edge detection algorithm, followed by a Hough transform to identify straight line segments within the midline strip of intracranial space.

The falx cerebri itself can be distorted (bent) in cases of midline shift, the straight line segments themselves sometimes cannot be reliably used to define the midline plane. In 308 of FIG. 3, points of intersection of the straight line segments with the inner table of the skull are determined. These points can then be used to define the expected normal plane of the falx.

A plane in three dimensions can be fit to these points using an iterative method such as Random Sample Consensus (RANSAC) that separates inliers from outliers (310). This defines the falx plane with high accuracy, because points contributed by spurious straight line segments that are not part of the falx are not included in the final fit model. Other algorithms for fitting a plane to a set of noisy data points in 3D space could also be utilized herein to locate the expected normal falx plane.

Figure 4:
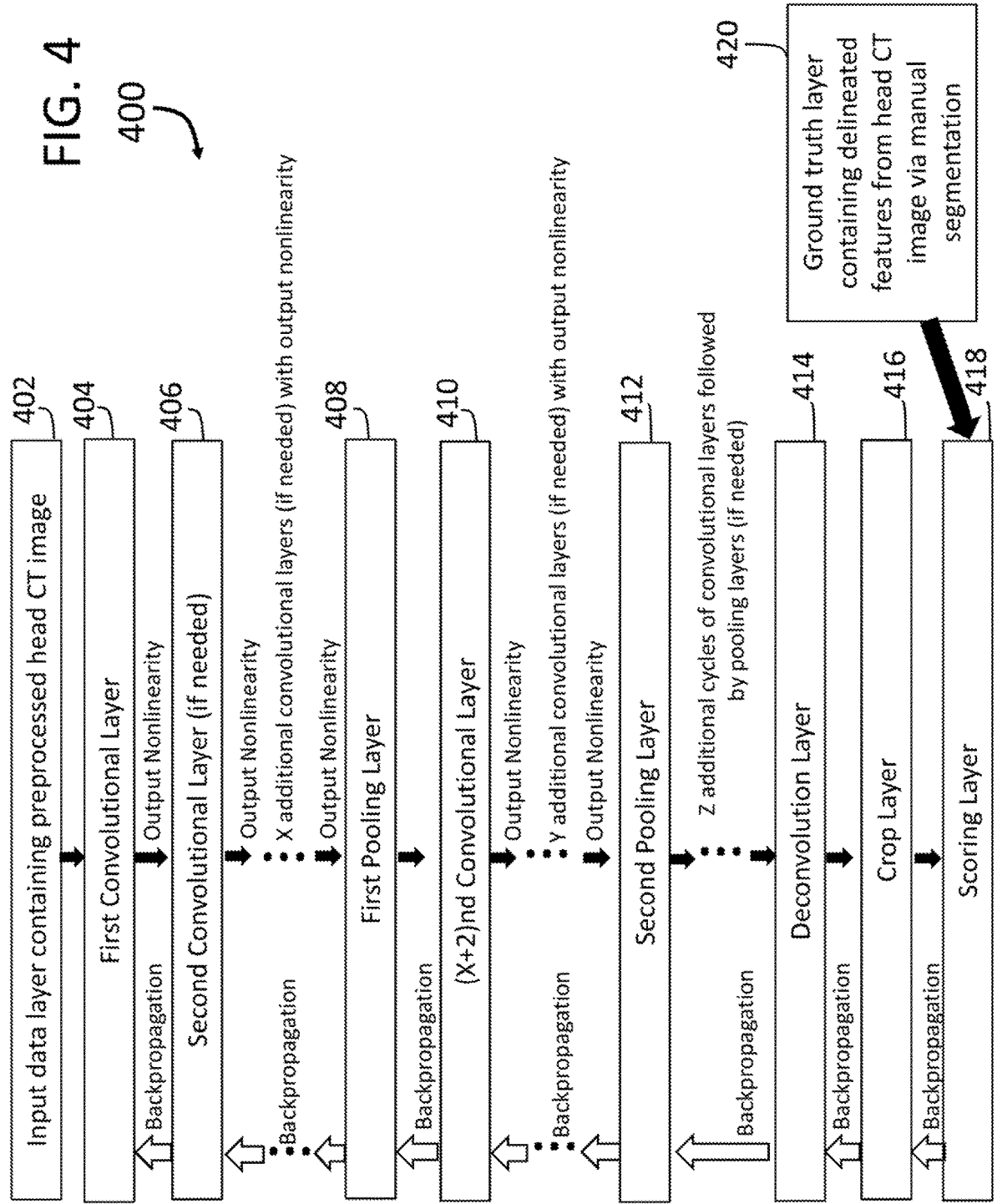
FIG. 4 shows a method for training a convolutional neural network to identify and localize intracranial hemorrhage or other features that may require emergency medical intervention.

To detect midline shift of the brain, in 312 (FIG. 3), the ventricular system is defined using identification of 3D-connected areas consisting of low CT-density pixels in the range of cerebrospinal fluid (approximately 0 to 15 Hounsfield units), and that exceed a volume of at least several cubic centimeters in order to reject smaller CSF-filled structures such as sulci. Alternatively, the ventricular system can also be identified using training of a CNN as shown in FIG. 4 and demonstrated in FIG. 17. Fully automated mapping of the ventricular system using a trained CNN relies on likelihood values that are the output of the CNN, and does not require CT density information as measured in Hounsfield units. Once the ventricular system has been delineated through either heuristic or CNN techniques, in 314 parameters that define the symmetry of the ventricular system (for example, but not limited to, the centroid of the ventricular system relative to the midline plane) are calculated. These can then be used to quantify the midline shift. An alternative method to quantify the midline shift is to demarcate the septum pellucidum using a CNN trained with manual segmentations of the septum pellucidum, and determining the maximum deviation of the septum relative to the falx plane.

Application of Convolutional Neural Networks

Returning now to FIG. 1, in 118 the areas, subtypes and volumes of intracranial hemorrhage are identified from the CT images. As is the case for other steps described herein, both heuristic and deep learning techniques can be performed for intracranial hemorrhage detection. In a preferred embodiment, a fully convolutional neural network (FCNN) is trained end-to-end using dense pixelwise labeling from manually segmented head CT data. An FCNN differs from standard convolutional neural networks in that it does not contain the fully connected layers that are typically found at or near the tops of standard CNNs.

Intracranial hemorrhage detectable by the human eye on CT images can take on sizes that range from approximately 1 millimeter to tens of centimeters in at least one dimension, and have a nearly endless variety of different morphologies. This problem is well-suited to dense pixelwise prediction using an approach that combines coarse and fine detail through combination of higher and lower layers of the fully convolutional neural network.

A way to achieve the analysis of 118 is shown in FIG. 4, which presents a flow-chart of steps in training an FCNN on CT image data.

The methodology herein applies FCNNs to head CT analysis in conjunction with the use of dense pixel labeling. Dense pixel labeling derived from manual segmentation of features of interest on head CT images, such as intracranial hemorrhage, is used to train the FCNN to identify and map the features. Although standard CNNs can potentially be trained to identify features such as intracranial hemorrhage or brain herniation on head CT using feedback on entire images, i.e., imagewise learning, an FCNN trained using dense pixelwise learning can be more efficient for this purpose in that many fewer example images are needed to train the network to the desired level of accuracy. For example, accurate detection and quantification of intracranial hemorrhage may be achieved by training the FCNN using dense pixelwise learning on as few as 1000 example head CT images preprocessed using the heuristic algorithm described in blocks 110, 112 and 114. Preferably the training set of images encompasses the desired broad range of subtypes of the pathology, such as epidural hemorrhages, subdural hemorrhages, intraparenchymal hemorrhages, hemorrhagic shear injury, and subarachnoid hemorrhages. Typically, training standard CNNs using only labels applied to entire images takes many more images to achieve accurate detection and, even in that case, may not accurately localize or quantify the feature of interest. To expand the set of training images for the FCNN, synthetic images can be generated by modifying an original image using transformations such as mirror reversal (i.e., reflecting left-right) or performing slight rotations of the images.

For training an FCNN using dense pixelwise learning, two inputs are used that together comprise the lowest two layers of the FCNN. The pixelwise image data forms one of the two lowest layers of the FCNN, known as the "image data layer" 402 that contains the pre-processed head CT image(s). The CT imaging data may be upsampled or downsampled in spatial resolution prior to entry as the image data layer for better performance of the overall FCNN. Similarly, the raw image data may be demeaned and/or rescaled to unit variance prior to entry as the image data layer for better performance. The image data may also be padded with additional pixels around its margins to achieve a desired dimension size, for example one that is an integer power of 2, in the image data layer (steps not shown).

The other input layer (besides the image data layer) at the bottom of the FCNN is the "ground truth layer" (feature map) 420, which contains binary data (0 or 1) at each pixel of the image data layer. The ground truth layer is derived from manual segmentation of the desired features in the image, e.g., acute hemorrhage on a head CT image, where zero (0) at a given pixel corresponds to absence of the feature at that pixel and one (1) corresponds to presence of the feature at that pixel. Alternatively, for the purpose of classification of image features, the ground truth layer may contain integer data (e.g., 0, 1, 2, . . . , n), where n is the number of feature classes, not including the absence of the feature, which is coded as zero (0). For example, different subtypes of hemorrhage are treated very differently clinically—some are rushed to surgery and others are considered to be not immediately life-threatening. Thus, intracranial hemorrhages can be manually labeled as 1 for subdural, 2 for subarachnoid, 3 for epidural, or 4 for intraparenchymal, where 0 would still indicate the absence of any type of hemorrhage at that pixel. This permits the FCNN to classify the type of hemorrhage, in addition to the presence or absence of a hemorrhage.

Manual segmentation and labeling of images can be performed by experts trained in the interpretation of CT images, by "crowdsourcing" or utilization of results from many expert or non-expert readers, by experts' correction of segmentations performed by less-experienced readers or by a computer algorithm, or by some combination of the above.

The image data layer and the ground truth data layer may consist of a single 2D image, a few adjacent 2D images that are each fed into separate channels of the FCNN, or a 3D image volume. Since many features that are desirable to detect are sparse, such as, for example, a small hemorrhage, this sparsity may give rise to a "class imbalance" problem where the training of the CNN is dominated by negative labels, i.e., pixels with ground truth values of zero (0), thereby reducing accuracy for detecting, localizing, quantifying and classifying positive features. To address this problem, only subsets of pixels with ground truth values of zero can be used for training, while the rest of the zero-valued pixels are not used for training. The number of zero-valued pixels used for training can be roughly matched to the number of pixels with positive ground truth values to address the class imbalance problem.

To train the FCNN to recognize features of interest on the head CT image, the data in the image data layer are then propagated through multiple interleaved convolutional and pooling layers in a computing process that is typical for feedforward CNNs. Unlike the data layers, all of the higher layers of the network are processing layers consisting of arrays of processing units that receive input from a lower layer or layers and send output to a higher layer or layers. Each "convolutional layer" (404, 406, and 410 in FIG. 4) performs local processing, which means that it uses only outputs of spatially adjacent processing units, and also contains an output nonlinearity, such as rectification, prior to its output being fed into a higher layer in the network. The most common output nonlinearity for CNNs is the "rectified linear unit" (ReLU), which is a piecewise linear function for which the output y=0 for input values x<0 and for which the output y=x for input values x>0.

After one or more layers of convolution with output nonlinearities, the data are fed into a "pooling layer" (408 and 412) that combines the output of multiple processing units in the layer below into a single output, thereby reducing the overall number of processing units in the pooled layer by a scalar factor. This may be viewed as a form of downsampling. Multiple cycles of convolution with output nonlinearity followed by pooling may be performed as the data are propagated through the entire network. After the final stage of pooling and convolution, the data are then deconvolved back to the original pixel size of the image data layer using a "deconvolution layer" 414 and are also registered to the same pixel locations of the image data layer using a "crop layer" 416.

Finally, the match between the output of the crop layer and the ground truth layer is determined using a standard accuracy metric, such as SoftMax with Loss, in the top layer of the network, which is a scoring layer (418). In order to train the FCNN, the degree of error in the scoring layer is then fed back down the network from the top to the bottom processing layer using the backpropagation algorithm (shown as arrows in FIG. 4), which adjusts the "weights", which are the strengths of the connections between processing units, in order to improve performance on the task.

Two related properties of the units of the FCNN that may be adjusted to improve feature detection and quantification accuracy are the "kernel" and the "receptive field". The kernel, also known as the "filter" or the "feature encoder", of a unit in the ith layer $F_i$ of the FCNN is the set of units in the previous layer $F_{i-1}$ that are directly connected to that unit. Therefore, the members of its kernel are the only units of $F_{i-1}$ that can directly modify the output of a unit in $F_i$. The kernel size of the unit in $F_i$ is expressed as the number of units along both dimensions (height and width) of the layer of $F_{i-1}$ contained in the kernel. For example, a unit with a kernel size of 3×3 is connected to three units along the height dimension and three units along the width dimension of the previous layer, for a total of nine connections.

It is conventional for the members of a kernel to be a contiguous rectangle of units in their layer, with no intervening units between them, unless a "dilation" factor greater than one is introduced, as explained elsewhere herein. The receptive field of a unit is the area of the image data layer (402) to which it is connected, either directly or through intervening layers of the FCNN. Therefore, the receptive field can be equivalently defined as the set of elements in the image data layer that modify the value of the unit. In the first convolutional layer (404), both the kernel size and the receptive field size of a unit are the area of the image data layer with which it is directly connected. For example, a unit in the first convolutional layer that is connected to a 3×3 square area of a 2D image data layer that has a single channel, representing a total of nine pixels of the single 2D image contained in the image data layer, has a kernel size and a receptive field size of 3×3. If the 2D image data layer has three channels instead, the receptive field size and kernel size of the unit remain 3×3, since the number of channels does not affect either property. Similarly, even if the image data layer is 3D, the kernel size and receptive field size of the unit remain 3×3 since only the height and width of the patch of the image data layer connected to the unit determine these two properties, not its depth. Beyond the first convolutional layer, the receptive field of a unit is larger than its kernel size since it includes not just the units of the previous layer that are in the unit's kernel but also all of the units in the receptive fields of those units of the previous layer.

Two properties that are specific to the units of pooling layers in an FCNN are the "pooling function" and the "stride". The pooling function is the mathematical operation used to combine the outputs of the units in the kernel of the unit of the pooling layer. The most commonly used pooling functions are "max" and "mean". A maxpooling layer is one in which the output of a unit is the maximum value of the outputs of all the units in its kernel. A meanpooling layer is one in which the output of a unit is the mean of the outputs of the units in its kernel. The stride factor is the number of units the kernel is shifted for adjacent units of the pooling layer. Thus, the stride factor is typically a positive integer. If the kernel size of all units of a pooling layer is 2×2 and the stride is 2, then the kernels of the pooling layer units will be non-overlapping. The width and height of the pooling layer will each be half that of the preceding layer, since the output of each non-overlapping 2×2 square of the preceding layer will be mapped onto a single unit of the pooling layer. If the stride factor is 1 instead, then the kernels of the pooling layer units will overlap along both height and width dimensions. The width and height of the pooling layer will each be only one unit less than that of the preceding layer. In general, for stride factors greater than one, the width and height of the pooling layer are the width and height, respectively, of the preceding layer divided by the stride factor.

To increase the accuracy of the FCNN for dense pixelwise learning of desired features, the property of "dilation" may be incorporated into one or more of its convolutional layers. Dilation expands the receptive field of the units of the convolutional layer without loss of spatial resolution or spatial coverage. This permits learning of features at larger spatial scales without incurring loss of spatial detail such as occurs with pooling with a stride factor greater than one. Dilation does not change the kernel size, but spreads out the units belonging to the kernel, thereby enlarging the receptive field. The degree of expansion of the receptive field depends on the dilation factor, which is a positive integer d that is typically chosen to be an integer power of two. The dilation factor describes the separation between two adjacent units in the convolutional layer $F_{i-1}$ that belong to the kernel of a unit in the next convolutional layer $F_i$. Therefore, a dilation factor of one (equal to $2^0$) is equivalent to a non-dilated convolution since units of the kernel that are nearest neighbors have no intervening units between them in their convolutional layer. A dilation factor of two (equal to $2^1$) means the units of the kernel that are nearest neighbors of each other have one intervening unit of the layer between them that does not belong to the kernel. A dilation factor of four (equal to $2^2$) means that nearest neighbor units of the kernel are separated by three intervening units of the layer that do not belong to the kernel. Hence, in the first convolutional layer (404), a unit with a dilation factor of 1 and a kernel size of 3×3 has a receptive field size of 3×3. In the second convolutional layer (406), a unit with a dilation factor of 2 and a kernel size of 3×3 has a receptive field size of 7×7. In the third convolutional layer, a unit with a dilation factor of 4 and a kernel size of 3×3 has a receptive field size of 15×15. In general, for an FCNN with a kernel size of 3×3 for the first convolutional layer $F_1$ and exponentially increasing dilation factors $2^{i-1}$ for each successive layer $F_i$, both the height and width of the receptive field of a unit in $F_{i+1}$ is $(2^{i+2}-1)$.

To increase the accuracy of CNNs for intracranial feature detection and for hemorrhagic feature classification, as well as to accelerate the training process to reach the optimal accuracy more quickly, "deep residual learning" may be employed. In this approach, the output of a convolutional layer $F_i$ may be added to the output of a later convolutional layer $F_{i+n}$, where n is typically two or three. Importantly, the addition occurs prior to the output nonlinearity (e.g., ReLU operation) of $F_{i+n}$. This addition, which occurs across non-consecutive convolutional layers, is also known as "identity shortcuts" since the additive outputs skip intervening layers. For very deep CNNs, i.e., those with dozens or hundreds of layers, these "residual networks" (ResNets) can obtain higher accuracies for feature detection and classification than very deep CNNs that do not have this additive configuration.

To accelerate the training time of a ResNet, a "bottleneck" configuration may be used for the intervening layer(s) between an identity shortcut. The bottleneck configuration interposes a convolutional layer with 1×1 kernel size both before and after the intervening layer(s) of the shortcut. The 1×1 layer before the shortcut has a channel dimension smaller than the preceding output layer that is to be added to the layer after the bottleneck, but equal to the intervening convolutional layer(s) to be skipped by the shortcut. The 1×1 layer after the intervening layers has a channel dimension equal to the layer after the shortcut, which is larger than the skipped layer(s). This bottleneck has the effect of reducing the overall computational burden by reducing the channel dimension of the intervening layers while still matching the channel dimensions of the layers before and after the shortcut so that their outputs can be added.

The optimization of the weights of the FCNN based on the training CT images can be performed with one of several optimization algorithms, the most widely used of which are the class known as gradient descent algorithms. A particularly effective choice of weight optimization algorithm for this application is stochastic gradient descent (SGD). This is because it is impractical to train the FCNN on all of the training images at once due to computer memory constraints. With SGD, the FCNN weight optimization may be performed using small batches of images at a time, in a technique known as "minibatch learning" or even as single images at a time, in a technique known as "online learning". This allows training of the FCNN within ordinary computer memory and processing power constraints.

The initial weights of CNNs can be set randomly in order to "train from scratch" with a specific training dataset. Alternatively, the weights from a CNN that has already been trained on a prior dataset may be used as the initial weights for training on the new dataset. This latter approach is known as "fine tuning" or as "transfer learning" and has the advantage that learned features from the prior dataset may be carried over to training on the new dataset, thereby accelerating the training as well as making the overall results more accurate. In order to learn emergency features on head CT scans, a CNN already trained with a dataset from a single or multiple type(s) of CT scanner model(s) and CT image acquisition protocol(s) can be fine-tuned by further training on a new dataset from a different type of CT scanner and/or CT image acquisition protocol. This would enable the fine-tuned CNN to achieve better performance on CT images acquired from the new type of CT scanner and/or new CT image acquisition protocol in terms of the accuracy of emergency feature detection, mapping and quantification. This transfer learning strategy would allow the system to keep pace with progress in CT scanner hardware and software for image acquisition.

Implementation on GPUs

For training CNNs, including FCNNs, the most effective computer architecture today contains one or more graphical processing units (GPUs), each of which contains many separate parallel processing units. A block diagram of a computer architecture containing a GPU is shown in FIG. 2. Because of its massive parallelism, the GPU can instantiate the many processing units of an FCNN much more efficiently than computer architectures based only on a central processing unit (CPU). This results in training speeds for a GPU-based system that can be orders of magnitude faster than a system containing one or a handful of CPUs. The GPU-based computing system can either be local in the form of a dedicated GPU workstation or GPU chip(s) incorporated into a personal computer, or it can be remote in the form of cloud-based GPU instances such as those available from the Amazon Web Services (AWS) Elastic Computing Cloud (EC2). Even using a GPU, training of an FCNN for detecting features on head CT images may require compute times of many hours, or even up to a day or more, depending on the number of training images and the processing power of the GPU. Training an FCNN on 3D volumes typically requires more computing time than on 2D images due to the larger volume of data.

To further accelerate CNN training on head CT image data, the weight optimization process may be distributed over many GPUs working in parallel across very high-bandwidth network connections to allow for efficient data transfer across GPUs. Such an arrangement can be instantiated on a local multi-GPU workstation such as the NVIDIA DevBox or as a cloud-based multi-GPU computing cluster such as the AWS EC2 Cloud Formation. There are two primary ways to accomplish "distributed deep learning" using multiple GPUs. One approach, known as "model parallelism", divides up the CNN model weights across the different GPUs, each to be trained on the same set of data, and then the outputs of each CNN model part are exchanged across the GPUs to determine the overall output of the CNN model. The other approach, known as "data parallelism", divides up the CT images in a batch across the different GPUs, each to be trained on the same whole CNN model, and then the weight gradient updates resulting from training on each subset of the batch are added up to determine the overall weight gradient updates for the entire batch of data. Model parallelism is more efficient for CNN architectures with large numbers of weights, such as those with fully-connected layers. Data parallelism is more efficient for CNNs with relatively small numbers of weights, such as FCNNs, especially when trained on large amounts of data. Distributed deep learning can be applied in layer-specific fashion, such that model parallelism is used for fully-connected layers of a CNN whereas data parallelism is used for convolutional layers.

To speed up training of an FCNN on a large CT image dataset, data parallelism across multiple GPUs is the most efficient strategy. This can be implemented using a distributed version of SGD that is "synchronous" across GPUs, in that the weight gradient updates on different images of the batch occur in parallel across the GPUs and, once completed, then those weight gradient updates are summed over the GPUs to derive the overall weight update for the entire batch. Only the weight gradient updates for the backward passes of the SGD optimization need to be summed across the GPUs. The weight gradient updates for the forward passes can occur on each GPU independently, as would occur for single-GPU training. The weight gradient updates for the backward passes can be summed across GPUs by a single GPU, called a "parameter server", which then communicates the summed weight gradient updates to all of the other GPUs to use for their copies of the FCNN model. The parameter server can become a communications bottleneck when training across large numbers of GPUs, since the communication time is proportional to the number of GPUs. In this case, it may be more efficient to employ a "reduction tree" approach in which the weight gradient summing is performed hierarchically across neighboring GPUs in the network in a bottom-up fashion and then the final summed gradients are propagated top-down to all the GPUs. The communication time for a reduction tree is proportional to the logarithm of the number of GPUs, where the base of the logarithm is the number of adjacent GPUs that sum weight gradients at each level of the hierarchy.

Applying a Trained FCNN to New Images

Figure 5:
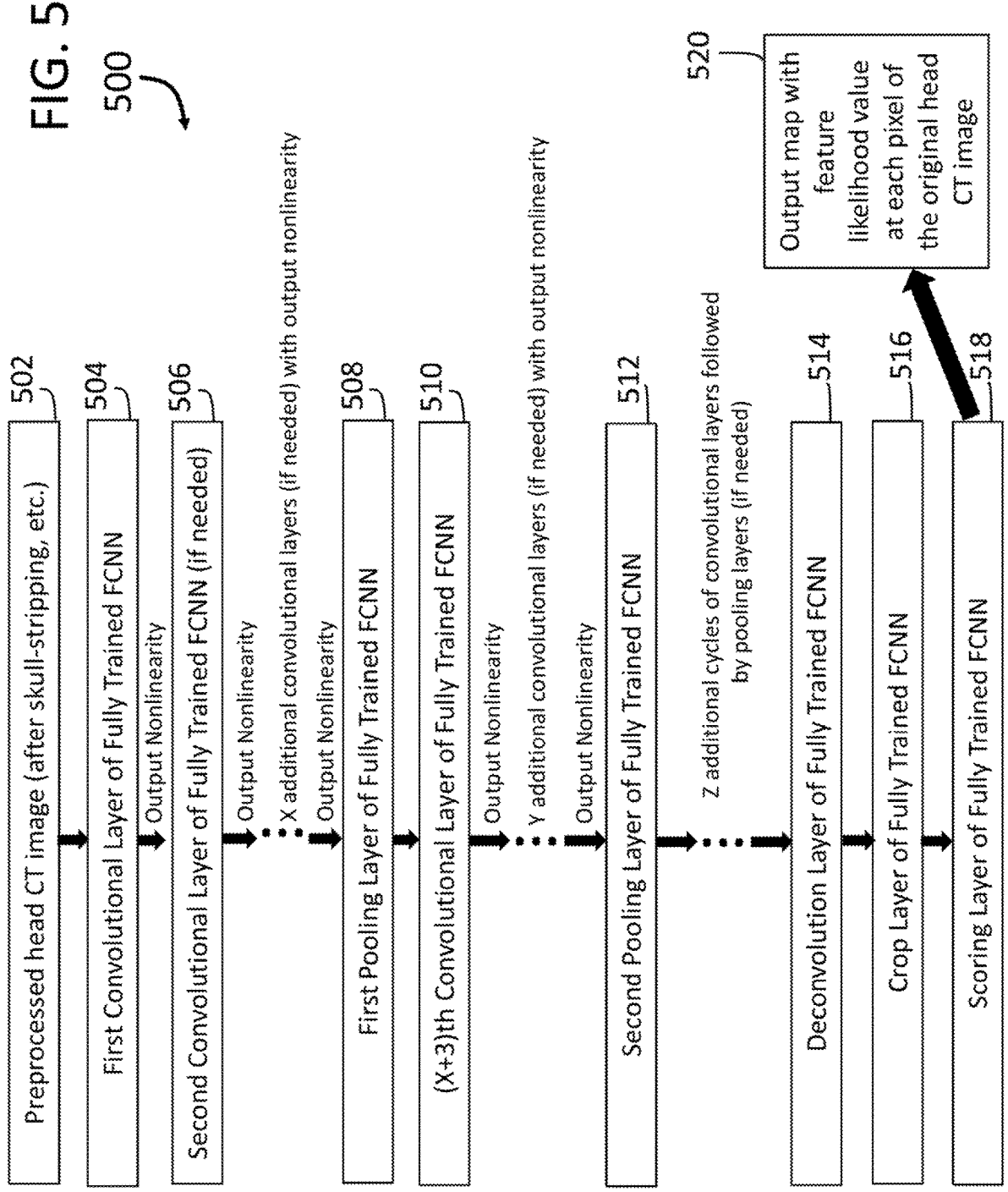
FIG. 5 shows a method for applying a trained convolutional neural network to localize intracranial hemorrhage or other emergency features.

As shown in FIG. 5, once trained on enough head CT images, the trained FCNN can then be used to evaluate head CT images different from those in its training set, e.g., in order to determine its accuracy for detecting the feature(s) of interest. This process is referred to as "testing." Review of its performance can be performed either quantitatively using the accuracy metric of the FCNN scoring layer, or qualitatively by visual interpretation of its output by an expert such as a radiologist. This process of applying the fully trained FCNN to new images (FIG. 5) is significantly faster than the process of training the FCNN (FIG. 4), and typically requires from only seconds to a few minutes. A GPU may not be required for fast performance of applying a trained FCNN. However, if multiple GPUs are available, it is straightforward to apply data parallelism to testing an FCNN since only forward passes are required and therefore the different GPUs can work on different images independently of each other.

The output of the FCNN is similar to the ground truth data except that, instead of a binary value at each pixel of the head CT image that represents the presence or absence of a given feature, there is a probability value that is a real number ranging from 0 to 1 that represents the likelihood of the feature being present at that pixel. The sum of the areas of all the pixels having a probability above a certain threshold ("supra-threshold pixels"), for example 0.7, can be used to measure the total area of the feature on the 2D image. Applied across adjacent 2D images, each of which has been classified by an FCNN trained to identify the feature on a pixelwise basis, the sum of the areas of the supra-threshold pixels multiplied by the thickness of a 2D image can be used to compute the volume of the feature within the 3D stack of images. This is because head CT images are usually reconstructed at a constant thickness across all the 2D images.

The accuracy of detection, mapping and quantification of emergency head CT features, such as acute intracranial hemorrhage, may be improved by employing ensembles of multiple fully trained CNNs instead of only a single fully trained CNN. The output of each CNN expressed as a probability, from 0 to 1, of the feature being present at each pixel can be averaged with the output of all of the other CNNs, and/or with other types of machine learning classifiers, to generate the overall probability for the feature at that pixel. Results from ensembles of CNNs may be more accurate than that of a single CNN, especially when the different CNNs of the ensemble have different network architectures and/or hyperparameters used during the training process, and therefore may have different strengths for the feature detection process which can be combined by using the whole ensemble of CNNs. As with data parallelism for testing fully trained CNNs, using an ensemble of fully trained CNNs also benefits from multiple GPUs operating in parallel, since each CNN can run on a separate GPU using the same testing data and then these results can be combined once the final output of each CNN is available. This is much faster than running each CNN sequentially on the same GPU. In addition to combining the results of the fully trained CNNs by simple averaging, more sophisticated methods are possible such as a weighted average that more strongly favors the results of CNNs known to have better accuracy for the desired feature than those known to be less accurate.

For the purpose of quantitation of feature characteristics such as size and CT density, the optimal threshold for determining the presence of a feature at a pixel from the FCNN-derived likelihood value is dependent on the particular feature to be detected and the distribution of likelihood values on the image. For the example of mapping intracranial hemorrhage with a well-trained FCNN using pixelwise learning, empirical evaluation of the histograms of the likelihood values by an expert radiologist typically yields an optimal threshold in the range of 0.6 to 0.8. Other alternative approaches for mapping the spatial extent of features using pixelwise likelihood values from a trained FCNN include automated threshold selection based on histogram characteristics as well as methods that do not require a fixed likelihood threshold but rather cluster contiguous pixels with high likelihood values, such as threshold-free cluster enhancement.

Besides size, another useful property of features on head CT scans that can be quantified using a trained FCNN is CT density, also known as x-ray attenuation, usually measured in Hounsfield units. Once the spatial extent of a feature has been mapped on a head CT image or set of images, the CT density of each pixel containing the feature can be determined from the original head CT image as the value of that pixel in Hounsfield units. This works because the pixels in the likelihood map that is the output of the trained FCNN remain in register with the pixels of the original head CT image. An example of the usefulness of CT density information is provided by intracranial hemorrhage, where the CT density of the blood in the hemorrhagic region usually indicates the acuity of the hemorrhage, where more recent hemorrhages usually have higher Hounsfield units than older bleeds, thereby providing useful information for the radiologist and the clinician.

As it will often be helpful to medical staff caring for the patient, as well as for research purposes, to know the anatomic location of abnormalities, in 124 this can be achieved by registering the brain to a standard CT or MRI brain atlas. This can be performed by several approaches, including registration of the head CT under evaluation to any of the following for which anatomic locations are available: 1) a "standard" head CT atlas, 2) a standard head CT for which there is a corresponding brain MRI, or 3) directly to a brain MRI. This process can be performed with any brain atlas, such as the Montreal Neurological Institute (MNI) atlas or any other segmented or labeled CT or MRI brain atlas. The algorithm used for registration of the head CT images can be one of several standard methods for affine transformation, i.e., translation, rotation, scaling and shearing, or nonlinear warping. Because in some cases the brain will be significantly distorted by the presence of abnormalities such as large intracranial hemorrhages or other lesions, making accurate registration to a standard atlas more difficult, more reliable landmarks such as the attachment of the falx to the skull, the dorsum sella, the orbits or globes, or other skull or facial landmarks that are rarely altered or displaced by the presence of pathological intracranial conditions, can be used to aid in registration.

Precise spatial location information from head CT scans (e.g., coordinates of a pixel), available after anatomic registration of the scans to a brain atlas, can also be useful to improve the accuracy of CNNs, including FCNNs, for detecting, mapping, and measuring emergency features. Some abnormalities are likely to occur at certain locations in the head, and the CNN can use that spatial information to improve its prediction of the presence or absence of an abnormality at a particular location. This can be achieved by, for example, incorporating three-dimensional atlas coordinates (x, y, and z) as features to be used in training the CNN.

For the case of an FCNN using dense pixel learning, the three spatial coordinates for each pixel of the image in the data layer could be added as three additional channels in the first convolutional layer of the FCNN (404 of FIG. 4), regardless of whether the image in the data layer is 2D or 3D. In this way, the output of the first convolutional layer will incorporate this precise spatial information. Alternatively, the x, y, and z spatial coordinates of each unit's receptive field center can be added as additional channels to a higher-level convolutional layer (e.g., FIG. 4 at 406 or 410). Pixel-level spatial coordinates can also be added directly to the final scoring layer (418), in which the overall error of the FCNN model is computed by comparison to the ground truth layer and used for weight adjustments back through the FCNN during a backward pass.

The improvement in performance for detecting, mapping and quantifying particular emergency features such as acute intracranial hemorrhage from adding spatial location information at lower levels versus higher levels of the FCNN is determined empirically. Spatial information used for CNN training is not limited to the three-dimensional x, y, and z spatial coordinates, but can also include other important location features that may be application-specific, such as distances to major brain anatomic landmarks. For example, since distance from the brain midline or from the inner table of the skull is often an important feature for emergency head CT analysis, this distance can be added for each pixel or for each unit of a convolutional layer as an additional channel to those used for the x, y, and z spatial coordinates. Furthermore, using the method described elsewhere herein and shown in FIG. 3 and FIG. 10, distance from the brain midline can also be determined without registration of the CT scan to a standard brain atlas. Therefore, some types of spatial information such as this can still be used for CNN training even if brain atlas registration should prove impossible due to scan image artifacts, such as in FIG. 10 and FIG. 12 and/or severe brain deformations that preclude transformation to standard brain atlas space.

Another type of CNN, besides the FCNN, that can be used for detection, localization and classification of emergency features on head CT scans is the region-based convolutional neural network (R-CNN). Compared to the FCNN with dense pixelwise labeling described in hereinabove, an advantage of the R-CNN is that it requires manual delineation of only the rough outlines of a feature, which could be as simple as drawing a box around it, rather than manual segmentation of all pixels contained in the feature. However, the R-CNN using this "bounding box" supervised training approach is not as accurate for localizing a feature or quantifying its size as is the FCNN with dense pixelwise labeling.

In its most effective and efficient implementation, the R-CNN consists of a region proposal network (RPN) in the form of an FCNN with additional layers of the full R-CNN that complete the task of feature detection, localization and classification. The RPN finds the boxes that contain features of interest. To do this, it divides the input image into overlapping segments called "anchor boxes" of multiple scales (i.e., box sizes) and multiple aspect ratios (i.e. ratios of box width to height). The entire image is covered by the anchor boxes of each scale and aspect ratio. For an input head CT image generally of 512×512 pixels, typical scales of the anchor boxes may be 32, 64 and 128 pixels, whereas typical aspect ratios would be 1:1, 2:1 and 1:2.

For supervised training, the RPN also takes as input "ground truth boxes" that are manually drawn on the image for each feature contained in the image. An anchor box with an intersection over union (IoU) overlap of greater than 0.7 with a ground truth box is considered "positive", where IoU is computed as the ratio of the number of pixels contained in the intersection of the two boxes with the number of pixels contained in the union of the two boxes. An anchor box can also be considered positive if it ranks among the top anchor boxes in terms of IoU with a ground truth box, where the percentage of such anchor boxes accepted as positive may vary with the particular feature detection task. An anchor box that does not have an IoU of greater than 0.3 with any ground truth box is considered "negative". These positive and negative labels for the anchor boxes are used to train the RPN and anchor boxes that do not qualify as positive or negative by these criteria do not receive a label and therefore do not contribute to the RPN training.

Training of the RPN, which is an FCNN, uses the same methods described hereinabove. The primary difference with the standard FCNN approach is that the scoring layer that determines the match between the proposed bounding box regions of the RPN and the ground truth boxes uses a different objective function than the typical SoftMax with Loss for an FCNN. The objective function (i.e. error) to be minimized for an RPN is the sum of the classification error and the regression error. The classification error captures the likelihood that each anchor box is positive, i.e. overlaps strongly with a ground truth box, whereas the regression error captures the difference in location along the x and y coordinates of the two-dimensional image of each positive anchor box and the ground truth box that it overlaps with. This "bounding box regression" method improves the localization accuracy of the overall R-CNN. Analogous to the FCNN with dense pixelwise labeling described hereinabove, the RPN can be trained with only a subset of the anchor boxes with negative labels to solve the class imbalance problem in cases where the positive anchor boxes are greatly outnumbered by the negative anchor boxes. Although ground truth boxes for R-CNN training are typically rectangular in shape, they can also be manually drawn as the shape of any irregular polygon. To delineate a feature across multiple adjacent 2D images for multi-channel 2D or full 3D supervised training, the ground truth boxes on each 2D image corresponding to the same feature would be assigned the same label. These ground truth boxes do not need to be the same size or shape across the 2D images.

In the R-CNN, the RPN is followed by a feature detection and classification network (FDCN), which can be combined with the RPN to form a single unified CNN. The FDCN takes as input the output of the RPN. The FDCN itself consists of convolutional and pooling layers like an FCNN and an RPN, but the output of this initial part of the FDCN forms the input for the final stage of the FDCN, which includes a maxpooling layer followed by one or more consecutive "fully connected" layers for further processing. A fully connected layer is one in which all the units have connections to all the units of the previous layer, whether that previous layer be convolutional, pooling or itself fully connected. The output of the final fully connected layer is then fed into both a multi-class SoftMax plus Loss layer for feature classification and another layer that performs bounding box regression for feature localization. The manually provided classification labels, for an arbitrary number of classes, for the feature in each ground truth box provides the data to train the classification SoftMax plus Loss layer. For example, a class label of 0 can be used for no hemorrhage, 1 for subdural hemorrhage, 2 for epidural hemorrhage 3 for subarachnoid hemorrhage, and 4 for intraparenchymal hemorrhage. This is analogous to multi-class classification for an FCNN with dense pixelwise labeling, except that a label only needs to be provided for every ground truth box rather than for every pixel that will be used for supervised training. As with the RPN, training of the FDCN uses the same methods described hereinabove. To achieve training of the overall R-CNN, the RPN and FDCN can be trained in alternating fashion, with the RPN trained first, and then its output used to train the FDCN. The trained FDCN is then used to initialize the RPN, and the iterative process repeats. Typically only one or a few iterations are needed to achieve optimum performance.

Figure 6:
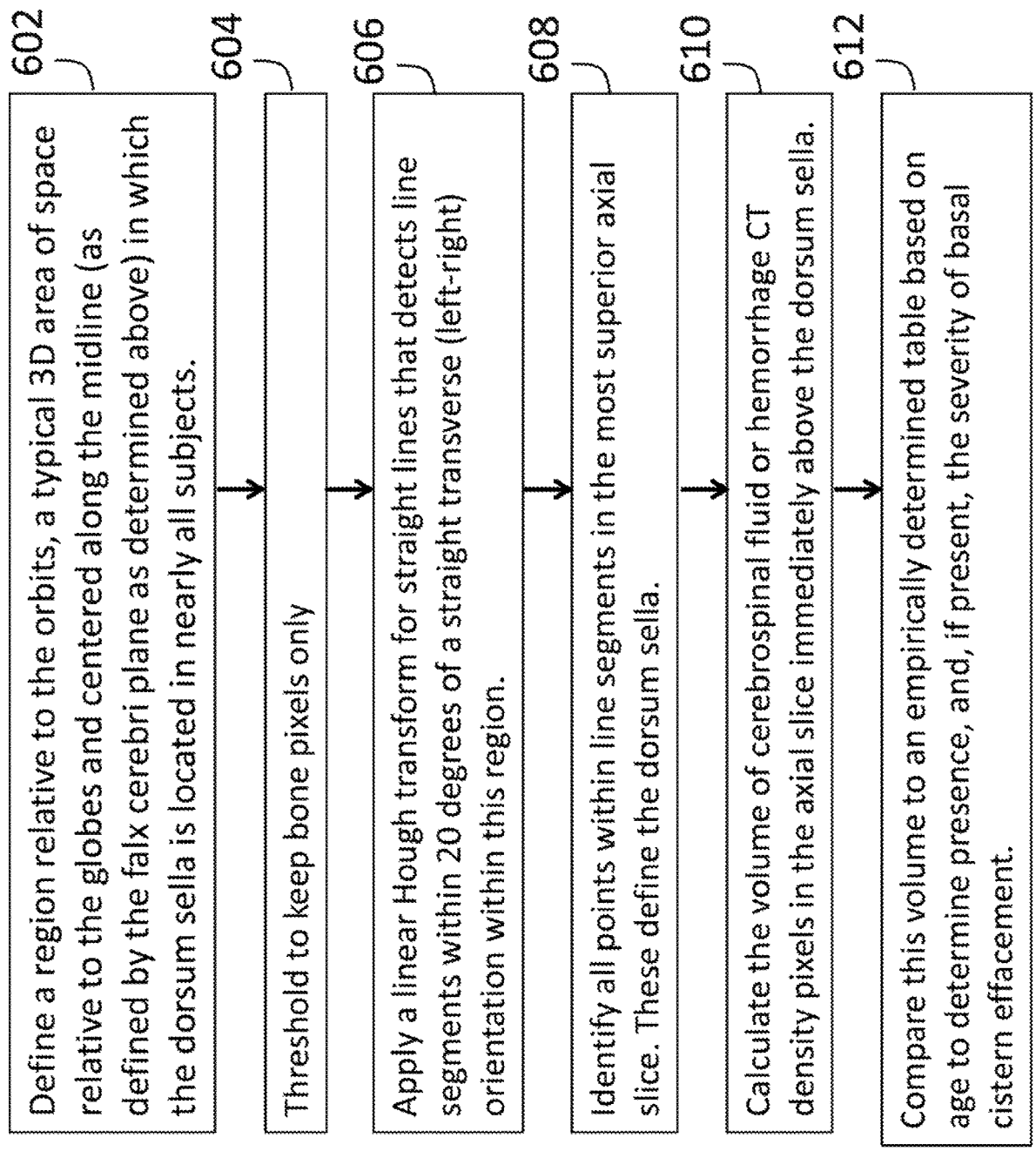
FIG. 6 shows a method for characterization of presence and degree of severity of downward cerebral herniation.

Downward cerebral herniation and uncal herniation are two other emergency features that may be encountered on head CT. In 120, these features are identified. FIG. 6 shows a block diagram of a heuristic algorithm for identifying and providing quantitative measures of these critical features. In the example heuristic algorithm in FIG. 6, the basilar cistern is located relative to surrounding structures at the skull base and then its volume is measured. The suprasellar cistern, referred to as the basilar cistern throughout this disclosure, is located by its relationship to the dorsum sella. The dorsum sella is a universal landmark within the skull base, and can be located by thresholding to keep only bone pixels (604), applying a linear Hough transform to the midline that detects line segments within 20 degrees of a straight transverse (left-right) orientation (606) within a typical 3D area of space, relative to the globes, that contains the dorsum sella (602). This process identifies the dorsum sella with high accuracy (608). The volume of the basilar cistern is then calculated (610). Alternatively, the basilar cistern can be identified and its volume quantified and morphology determined by training an FCNN using dense pixelwise labeling from manual segmentations of the basilar cistern. The process of training an FCNN using dense pixelwise labeling is described hereinabove.

In 126, quantitative summary parameters are calculated, for all head CT exams or selectable by the user based on clinical indication for a CT exam. The Marshall and Rotterdam CT scores, for example, may be calculated for head CT exams performed for a clinical indication of head trauma/suspected traumatic intracranial injury.

In 128, a summary report is generated, for all CT exams or with format selectable by the user based on clinical indication for a particular CT exam. For example, a report that follows the format of a standard radiological interpretation can be generated, with an option of editing by the radiologist or clinician prior to finalization, e.g., for the medical record.

Exemplary Computational Implementations

The methods described herein are preferably implemented as instructions run as software on one or more computer systems, and the implementation is within the capability of those skilled in the art of computer image processing. In particular, the computer functions for manipulations of CT data described herein can be developed by a programmer skilled in the art of data and image processing. The functions can be implemented in a number and variety of programming languages including, in some cases, mixed implementations (i.e., relying on separate portions written in more than one computing language suitably configured to communicate with one another). For example, the functions, as well as any required scripting functions, can be programmed in C, C++, Java, JavaScript, VisualBasic, Tcl/Tk, Python, Perl, .Net languages such as C#, and other equivalent languages. Certain mathematical functions for image processing can be written in scientific programming languages, and are preferably implemented in a form that takes advantage of a GPU. The capability of the technology is not limited by or dependent on the underlying programming language used for implementation or control of access to the basic functions. Alternatively, the functionality can be implemented from higher level functions such as toolkits that rely on previously developed functions for manipulating three-dimensional image data.

The technology herein can be developed to run with any of the well-known computer operating systems in use today, as well as others not listed herein. Those operating systems include, but are not limited to: Windows (including variants such as Windows XP, Windows95, Windows2000, Windows Vista, Windows 7, Windows 8 (including various updates known as Windows 8.1, etc.), and Windows 10, available from Microsoft Corporation); Apple iOS (including variants such as iOS3, iOS4, and iOS5, iOS6, iOS7, iOS8, iOS9, iOS10, and intervening updates to the same); Apple Macintosh operating systems such as OS9, OS 10.x, OS X (including variants known as "Leopard", "Snow Leopard", "Mountain Lion", "Lion", "Tiger", "Panther", "Jaguar", "Puma", "Cheetah", "Mavericks", "Yosemite" and "El Capitan"; the UNIX operating system (e.g., Berkeley Standard version) and variants such as IRIX, ULTRIX, and AIX; Google Chrome, and Android OS versions; and the Linux operating system (e.g., available from Red Hat Computing as well as open source distributions such as Ubuntu).

To the extent that a given implementation relies on other software components, already implemented, such as functions for manipulating three dimensional image data, and functions for calculating aspects of fitting mathematical forms to the same, as well as functions for implementing aspects of neural networks and of deep learning methods, those functions can be assumed to be accessible to a programmer of skill in the art.

Furthermore, it is to be understood that the executable instructions that cause a suitably-programmed computer to execute methods for analyzing CT data, as described herein, can be stored and delivered in any suitable computer-readable format. This can include, but is not limited to, a portable readable drive, such as a large capacity (for example, 0.5 TB, 1 TB, 2 TB or more) "hard-drive", or a "pen-drive", such as can be connected to a computer's USB port, an internal drive to a computer, a CD-ROM, a DVD-ROM, or an optical disk. It is further to be understood that while the executable instructions can be stored on a portable computer-readable medium and delivered in such tangible form to a purchaser or user, the executable instructions can be downloaded from a remote location to the user's computer, such as via an Internet connection which itself may rely in part on a wireless technology such as Wi-Fi. Such an aspect of the technology does not imply that the executable instructions take the form of a signal or other non-tangible embodiment. The executable instructions may also be executed as part of a "virtual machine" implementation, which may be local or in a remote location such as a data center that is part of a public, private or hybrid cloud.

The programmatic implementation of the methods herein on one or more computing apparatus includes also the implementation of functions that communicate with a medical imaging device such as a CT scanner. Thus, an exemplary implementation may be suitably configured to accept data directly from a CT scanner, and direct its output back to the imaging device or directly to a medical professional or technician. In this way, the methods as implemented herein lead to an improved performance of the CT scanner because the scanner can provide meaningful analysis of images where previously it could only display them in a form for further review by a medical professional.

EXAMPLES

Example 1

Figure 7:
FIG. 7 shows an example application of a system described herein for detection of a large intraparenchymal hemorrhage such as in a hemorrhagic stroke (FIG. 7A: Automated demarcation of abnormality.

Rapid detection of large intraparenchymal hemorrhage, as in hemorrhagic stroke (FIG. 7).

The CT image pictured in the center of FIG. 7 (panel B) was preprocessed in order to remove the skull and extracranial tissues using methods as described elsewhere herein. The preprocessed CT images, comprised of 512×512 pixels, were entered in the image data layer of a trained FCNN of the type shown in FIG. 5 and described hereinabove. The FCNN architecture further consists of two convolutional layers as shown in 504 and 506, each with a ReLU output nonlinearity, followed a pooling layer as shown in 508. By pooling adjacent inputs from the previous layer, the output of this first pooling layer was 256×256 pixels. The output of the pooling layer was then fed into two additional convolutional layers, each with a ReLU output nonlinearity, as shown in 510 where X=0 and Y=1. The output of these $3^{rd}$ and $4^{th}$ convolutional layers was then fed into a second pooling layer, as shown in 512, thereby reducing the pixel dimensions to 128×128. This was followed by three additional convolutional layers (Z=3 in FIG. 5). The output of the final ($7^{th}$) convolutional layer was then fed into the deconvolution layer, as shown in 514, which upsampled the image back to 512×512 pixels, followed by a crop layer, as shown in 516, which registered the output to the same pixel locations as the preprocessed image in the image data layer (502). The crop layer output was then converted in the scoring layer to a map of likelihood values of the presence of the feature at each pixel, as shown in the left-sided image of FIG. 7 on a graded blue (zero) to red (one) color scale, where zero indicates certainty that the feature is absent at that location and one indicates certainty that the feature is present at that location. This color scheme is depicted only as shades of gray on this grayscale figure. The FCNN output can be compared visually with the manual demarcation of the feature (shown on the right side of FIG. 7) by a neuroradiologist certified by the American Board of Radiology using a binary blue-red color scheme, where zero indicates absence of the feature and red indicates presence of the feature. This color scheme is depicted only as shades of gray on this grayscale figure. The probability map generated by the system depicted in FIG. 5 can be used to measure characteristics of the feature, such as size and CT density, using the methods described hereinabove. The CT image preprocessing and FCNN testing was carried out on a MacBook Pro 2014 edition running OS X Yosemite. The total compute time was under 5 minutes.

The FCNN described above was trained using the methods reported hereinabove, and depicted in FIG. 4. Initial weights between the processing units across the layers of the FCNN were set by randomly sampling Gaussian data with variance depending on the fan-in or fan-out of the processing units. The training of the FCNN to detect and map intracranial hemorrhage was performed using 60 head CT images containing acute hemorrhages of different subtypes (intraparenchymal, subarachnoid, subdural and epidural), sizes, shapes and numbers. For each original CT image, a synthetic image was generated by left-right reversal, thereby increasing the total number of training images to 120. For each training image, the crop layer output (416) was compared in the scoring layer (418) to the demarcation of the feature in the head CT image produced by a board-certified neuroradiologist (420), where the pixel is a binary value of one if the radiologist believes the feature is present at that location or a binary value of zero if the radiologist feels that the feature is absent at that location. This "ground truth" feature map was fed into the ground truth data layer of the FCNN. The scoring was done using a normalized exponential function in a logarithmic loss regime, known as "Soft-Max with Loss", which yielded a mismatch error value at each pixel between the crop layer output and the ground truth feature map. The final score from the mismatch error map was then used to reset the weights of the preceding layers of the FCNN using backpropagation (FIG. 4) with optimization of the network weights using stochastic gradient descent, a process consistent with supervised learning. The FCNN training was performed on an AWS EC2 g2.8xlarge GPU instance running Ubuntu Linux 14.04 using online learning (one image per batch) with a learning rate of 0.001 and a momentum of 0.9 for the stochastic gradient descent optimization. The total computation time for training the FCNN to detect and map intracranial hemorrhage on head CT images using this procedure was approximately 20 hours.

Example 2

Rapid detection of subdural hematoma, as in head trauma/traumatic intracranial injury (FIG. 8).

The head CT image in the center of FIG. 8 (Panel B) was analyzed using the identical procedure described in the previous example, using the same preprocessing and the same FCNN trained in the same way. As in FIG. 7, there is good correspondence between the likelihood map obtained in automated fashion (panel A) and the expert manual demarcation of the feature (panel C).

Example 3

Figure 9:
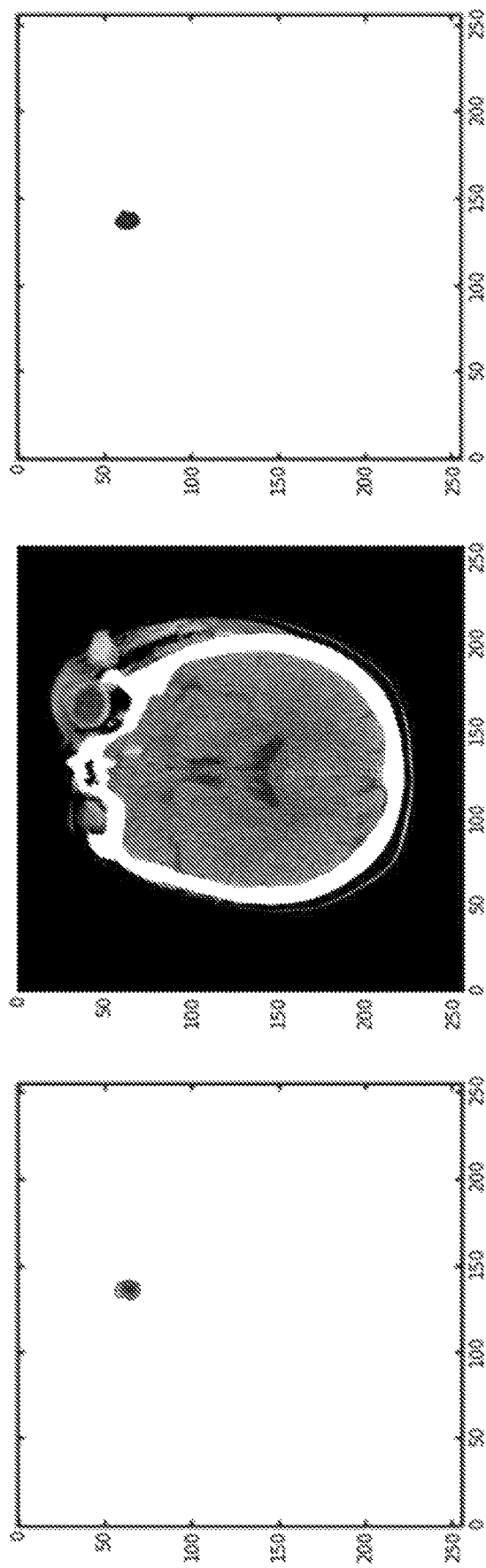
FIG. 9 shows an example application of a system described herein for detection of a small intraparenchymal hemorrhage (FIG. 9A: Automated demarcation of abnormality.

Rapid detection of small intraparenchymal hemorrhage (FIG. 9).

The head CT image in the center of FIG. 9 (panel B) was analyzed using the identical procedure as in the previous two examples. It can be observed that even small hemorrhages can be automatically detected and mapped by this procedure.

Example 4

Figure 10:
FIG. 10 shows an example application of a system described herein for detection of cerebral midline shift, as implemented in a cloud-based computer environment (in this particular case with user interaction through a website)

Automated detection and mapping of the midline of the brain (FIG. 10).

FIG. 10 shows a view of a user interface to a computer product that carries out computations as described elsewhere herein. At the right side of the central display of the interface is a sidebar with user controls. The original (unprocessed) head CT image is on the left side of the large display area of FIG. 10. The same image is on the right side of the large display area, and shows the midline of the brain demarcated by an overlaid straight white line. This demarcation was performed in fully automated fashion using the approach described in FIG. 3 as well as the description hereinabove that accompanies FIG. 3. Despite the extensive streak artifact on the top half of the CT image, as well as the tilt of the head with respect to the vertical axis, the midline of the brain can still be automatically identified with this method.

This automated midline detection function is implemented on a custom-designed website for "Interpretation and Quantitation of Emergency Features on Head CT Scans" that runs in the cloud on an AWS EC2 g2.8xlarge GPU instance running Ubuntu Linux 14.04, as also the case for the FCNN training described in Example 1. The website permits the user to upload head CT scans (de-identified for privacy reasons) for processing, and has the capability to store and display different patient scans as different cases. The brightness, contrast and magnification ("Zoom") of the CT images can be adjusted with the slider controls in the center of the right sidebar, or reset to the default values by clicking on the "Restore Defaults" button. The patient scan can be deleted from the website by clicking on the "Delete" button at the bottom of the right sidebar.

Example 5

Figure 11:
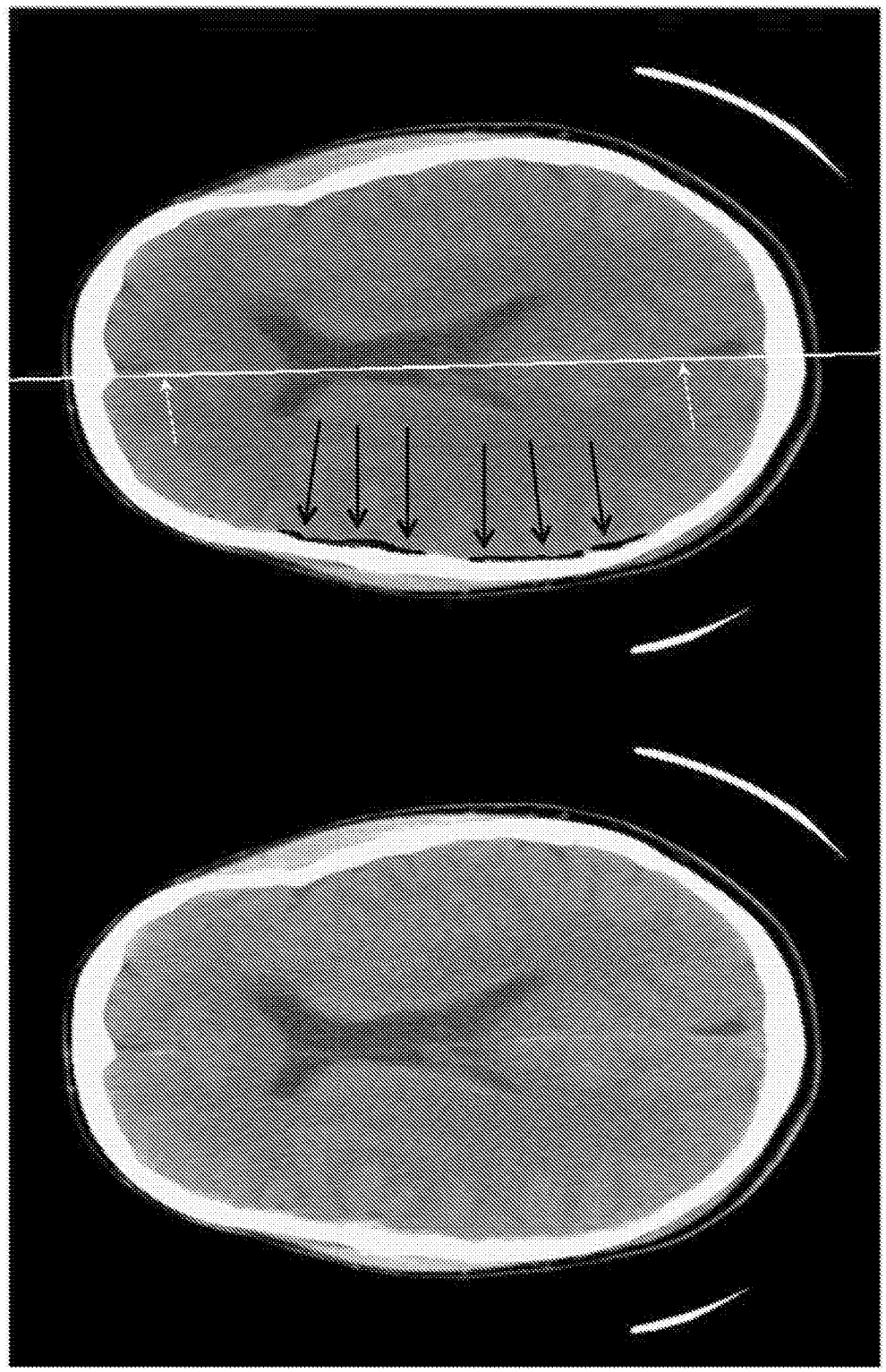
FIG. 11 shows an example application of a system described herein for detection of a very thin subdural hemorrhage.

Rapid detection and mapping of a small acute subdural hemorrhage (FIG. 11).

The original head CT image is on the left side of FIG. 11. The same image is on the right side of the Figure with the midline of the brain demarcated by an overlaid straight white line (marked by small dashed white arrows) and with a subtle thin acute subdural hemorrhage demarcated in black on this grayscale figure. In actual implementation, this hemorrhage would be demarcated in a bright color for easy visibility against the grayscale background of the CT scan. The midline demarcation was performed in fully automated fashion, as explained in Example 4. The fully automated mapping of the acute hemorrhage is as explained in Example 1, except for the following differences. Instead of the CT image processing taking place on a local computer, it takes place in the cloud on an AWS EC2 g2.8xlarge GPU instance running Ubuntu Linux 14.04, as also used in Example 4. Furthermore, as an elaboration of the FCNN architecture described in Example 1 and illustrated in FIG. 5, the FCNN architecture implemented for the current example in the cloud also incorporates dilated receptive fields as described hereinabove.

Example 6

Figure 12:
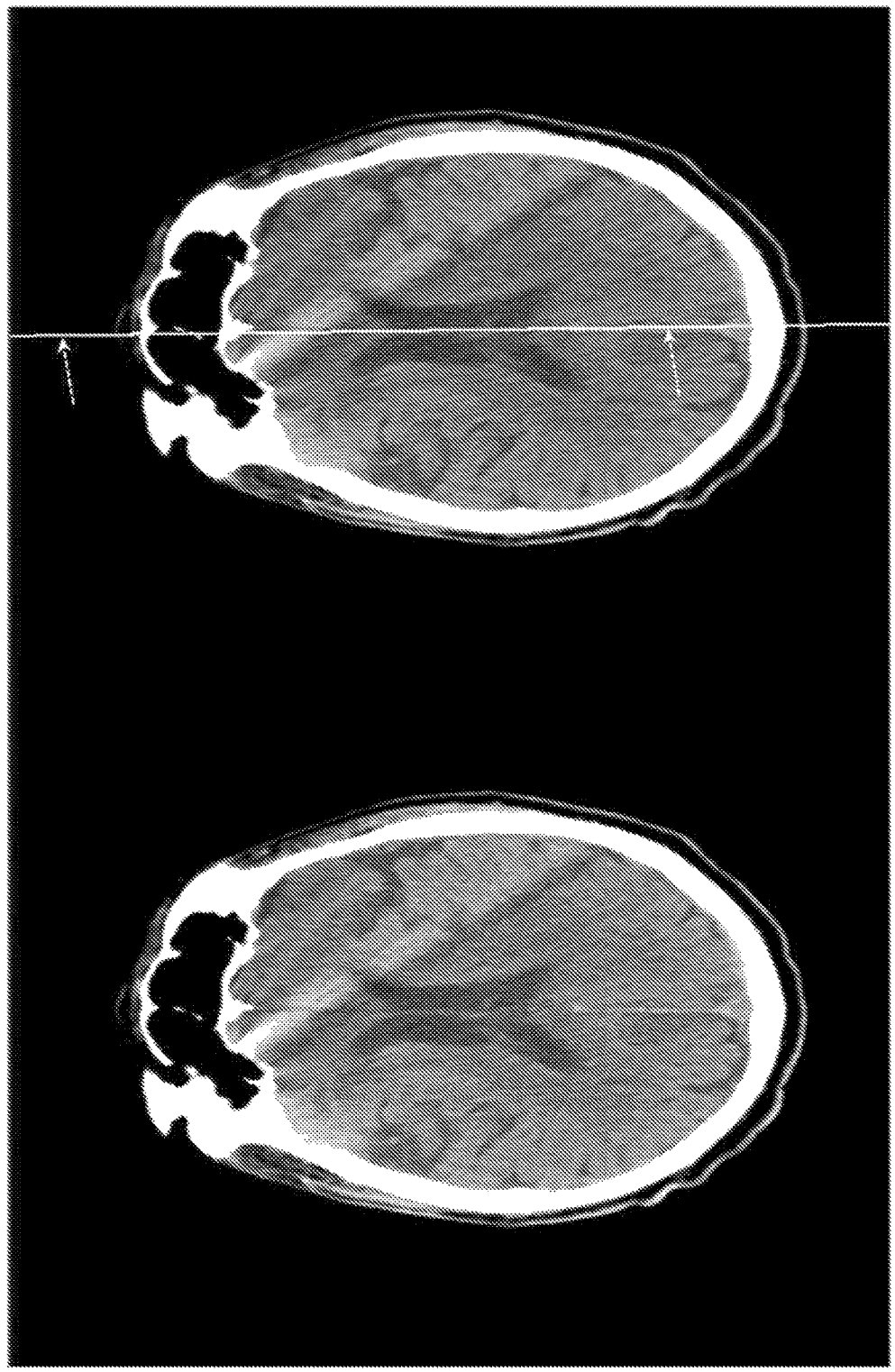
FIG. 12 shows an example application of a system described herein for detection of hemorrhage, in which the detection is accurate even in the presence of image artifacts.

Exclusion of acute hemorrhage in the presence of CT image artifacts from the presence of metal (FIG. 12).

The original head CT image is on the left side of FIG. 12. The postprocessed image is on the right side of the figure with the midline of the brain demarcated by an overlaid straight white line, marked by small dashed white arrows. The midline demarcation was performed in fully automated fashion, as explained in Example 4. No acute hemorrhage was detected by the same automated process as described in Example 5; therefore no parts of the right-sided CT image are designated as areas of intracranial hemorrhage by the automated algorithm. This is despite the presence of streak artifact in the upper part of the image from the presence of metal near that location which gives parts of the brain an apparent CT density similar to that of acute blood, even though no blood is actually present. Therefore the automated hemorrhage detection algorithm can correctly handle cases like these where there may be erroneous identification of acute bleeding by less experienced human evaluators of head CT scans.

Example 7

Figure 13:
FIG. 13 shows an example application of a system described herein for detection of the basilar cistern.

Rapid detection and mapping of the basilar cistern (FIG. 13).

The original head CT image is on the left side of FIG. 13. The postprocessed image is on the right side of the figure with the midline of the brain demarcated by an overlaid straight white line and the area of the basilar cistern is demarcated in white and is labeled with short thick arrows for the purposes of this grayscale figure. In actual implementation, this hemorrhage would be demarcated in a bright color for easy visibility against the grayscale background of the CT scan. The midline demarcation is performed in fully automated fashion, as explained in Example 4. The basilar cistern mapping is performed by the fully automated heuristic algorithm described in FIG. 6 and the accompanying description. As with the automated processes for detection and mapping of the brain midline and of acute hemorrhage, this process for detecting and mapping the basilar cistern is implemented in the cloud on an AWS EC2 g2.8xlarge GPU instance running Ubuntu Linux 14.04.

Example 8

Figure 14:
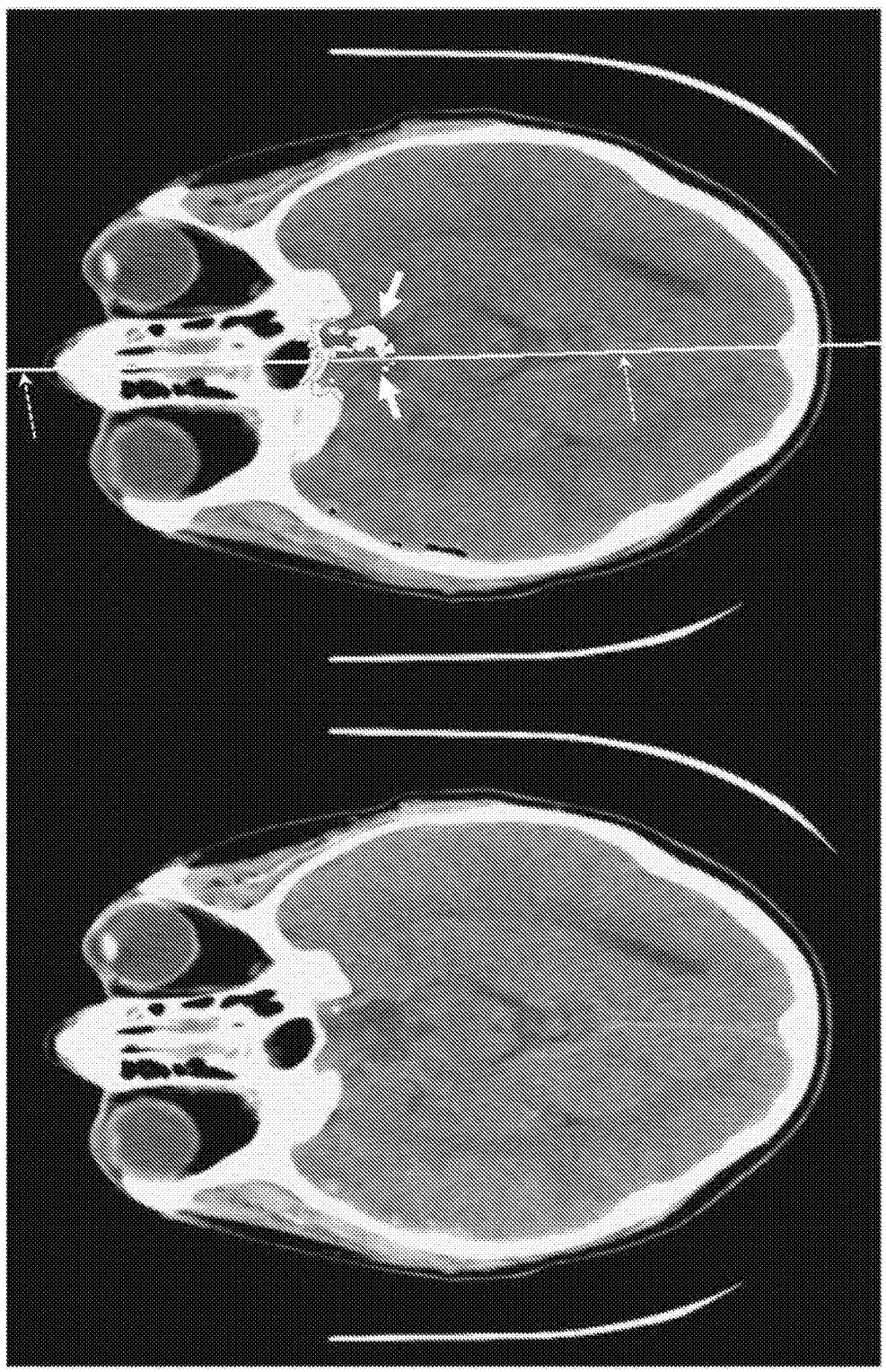
FIG. 14 shows an example application of a system described herein for detection of hemorrhagic contusions and downward cerebral herniation.

Rapid detection and mapping of acute hemorrhagic contusions and of downward uncal brain herniation with reduced area of the basilar cistern (FIG. 14).

The original head CT image is on the left side of FIG. 14. The postprocessed image is on the right side of the figure with the midline of the brain demarcated by an overlaid straight white line, the areas of acute hemorrhage due to brain contusions demarcated in black, and the basilar cistern demarcated in white. The midline demarcation was performed in fully automated fashion, as explained in Example 4, as was the demarcation of the hemorrhages, as explained in Example 5. The demarcation of the basilar cistern was performed in a fully automated fashion, as explained in Example 7. In the current example, the area and symmetry of the basilar cistern are decreased compared to the normal configuration illustrated in FIG. 13, due to downward herniation of the right temporal lobe because of brain swelling and/or space-occupying mass lesion(s). Downward herniation can represent a life-threatening emergency that may possibly require surgery depending on the reason for the herniation.

Example 9

Figure 15:
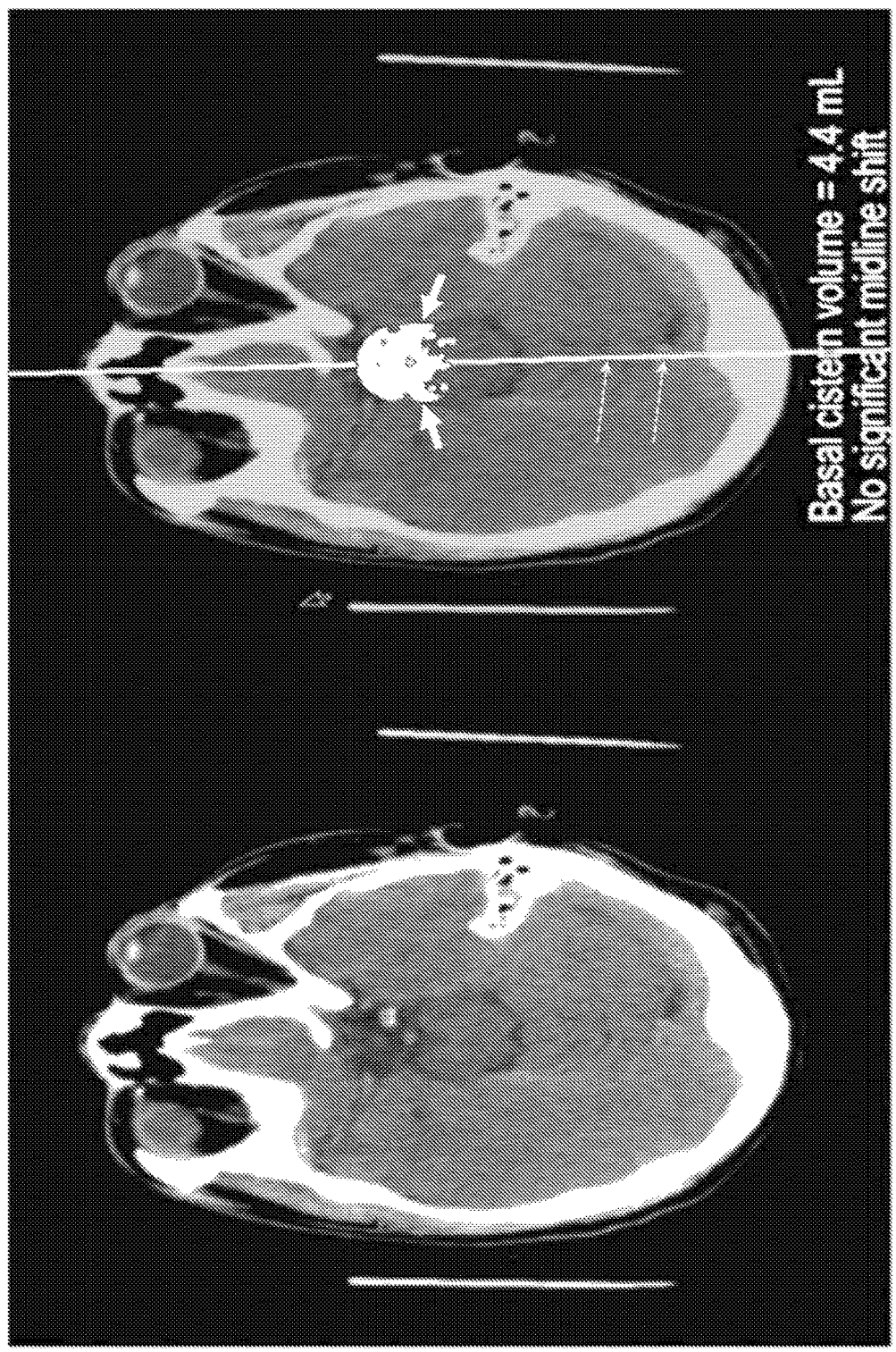
FIG. 15 shows an example application of a system described herein for detection and quantification of cerebral midline shift and basilar cisternal volume using heuristic algorithms.

Rapid detection, mapping and measurement of the basilar cisternal volume and of the midline shift using heuristic algorithms (FIG. 15).

The original head CT image is on the left side of FIG. 15. The postprocessed image is on the right side of the figure with the midline of the brain demarcated by an overlaid straight white line and marked by small dashed white arrows and the area of the basilar cistern demarcated in white and marked by short thick white arrows. The midline demarcation is performed in fully automated fashion, as explained in Example 4, as is the demarcation of the basilar cistern, as explained in Example 7. From the demarcated area of the basilar cistern, its volume can be computed by summing the area of the pixels of the image included in the demarcation of the basilar cistern and then multiplying this sum by the image thickness, which is a parameter of the CT scan acquisition. Typical units for this volume would be cubic centimeters, also known as milliliters (mL). In the current example, the basilar cistern measures 4.4 mL, as shown below the right-sided CT image. This value is computed by the automated heuristic process that demarcates the basilar cistern, as implemented on the cloud-based system described in Example 4. Similarly, the distance corresponding to how much the anatomic structures that should be located at the brain midline have been shifted away from the midline by brain swelling and/or space-occupying mass lesion(s), can also be automatically measured and displayed. When this midline shift is large, this may represent a life-threatening emergency that may require urgent surgery. The automated process for measuring midline shift in this example is explained in FIG. 3. In this example, the calculated midline shift is less than 5 millimeters (mm) and is therefore displayed below the right-sided CT image as "No significant midline shift". For cases of midline shift greater than 5 mm, the actual measured midline shift may be displayed instead. These measured volumes of the basilar cistern and distances of midline shift can be considered quantitative "biomarkers" of brain herniation that can be used for patient diagnosis and prognosis.

Example 10

Figure 16:
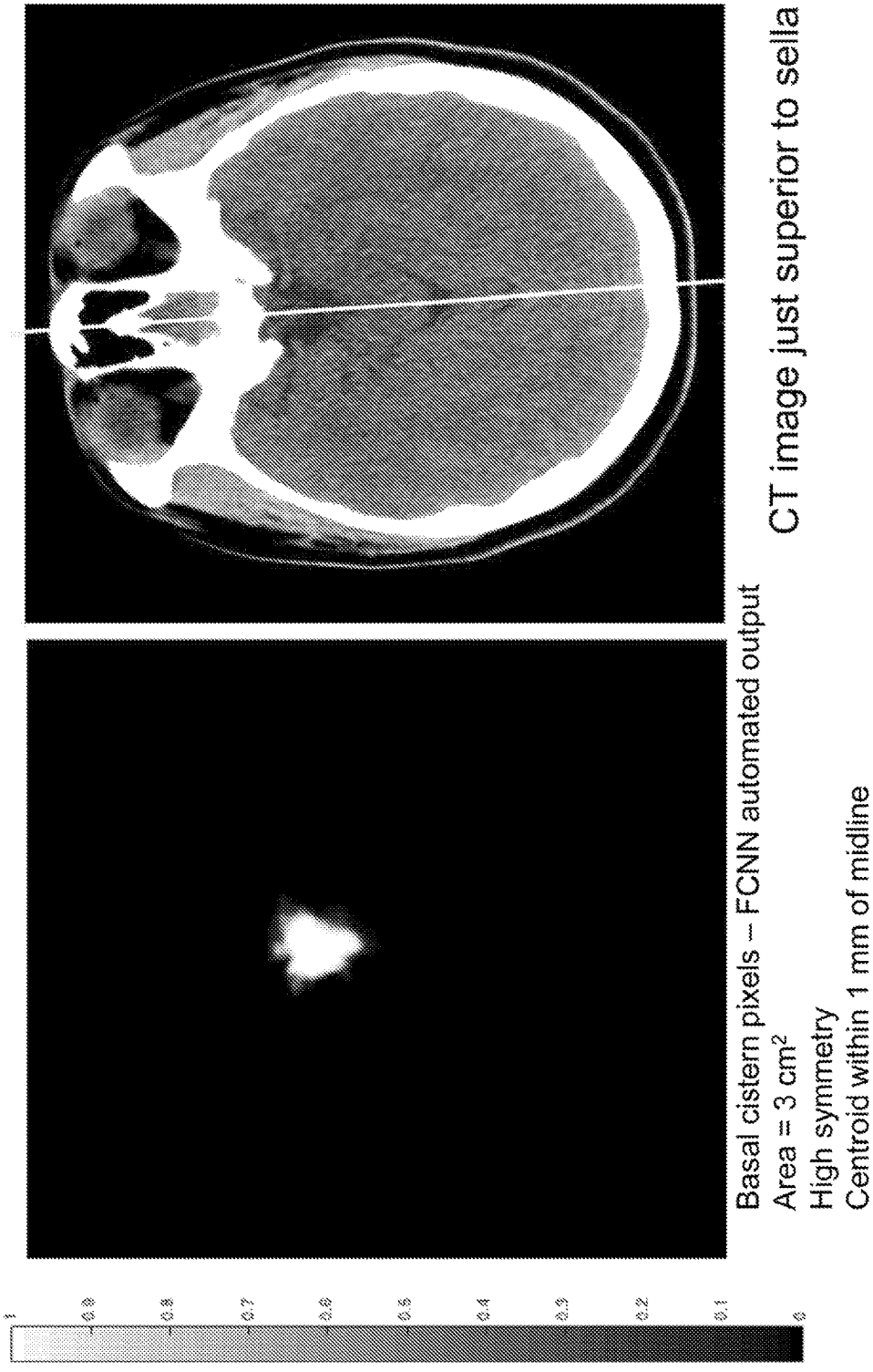
FIG. 16 shows an example application of a system described herein for detection and localization of the basilar cistern and assessment of its morphology and volume for evidence of downward cerebral herniation, using a fully convolutional neural network.

Rapid detection, mapping and measurement of the basilar cisternal area using an FCNN trained with dense pixel labeling and of the midline shift using a heuristic algorithm (FIG. 16).

The original head CT image is on the right side of FIG. 16 with the midline demarcated with a straight white line. The postprocessed image is on the left side of the figure. The basilar cistern is demarcated in fully automated fashion using an FCNN after the FCNN has been trained with dense pixelwise labeling from manual segmentations of the basilar cistern. The FCNN demarcation of the basilar cistern relies on the likelihood values that are the output of the FCNN (as shown on the scale bar at the left side of the figure) and does not require the actual CT density values (Hounsfield units). In this figure, the area of the basilar cistern on this slice is computed by summing the area of the pixels of the image included in the demarcation of the basilar cistern and is given in square centimeters.

Example 11

Figure 17:
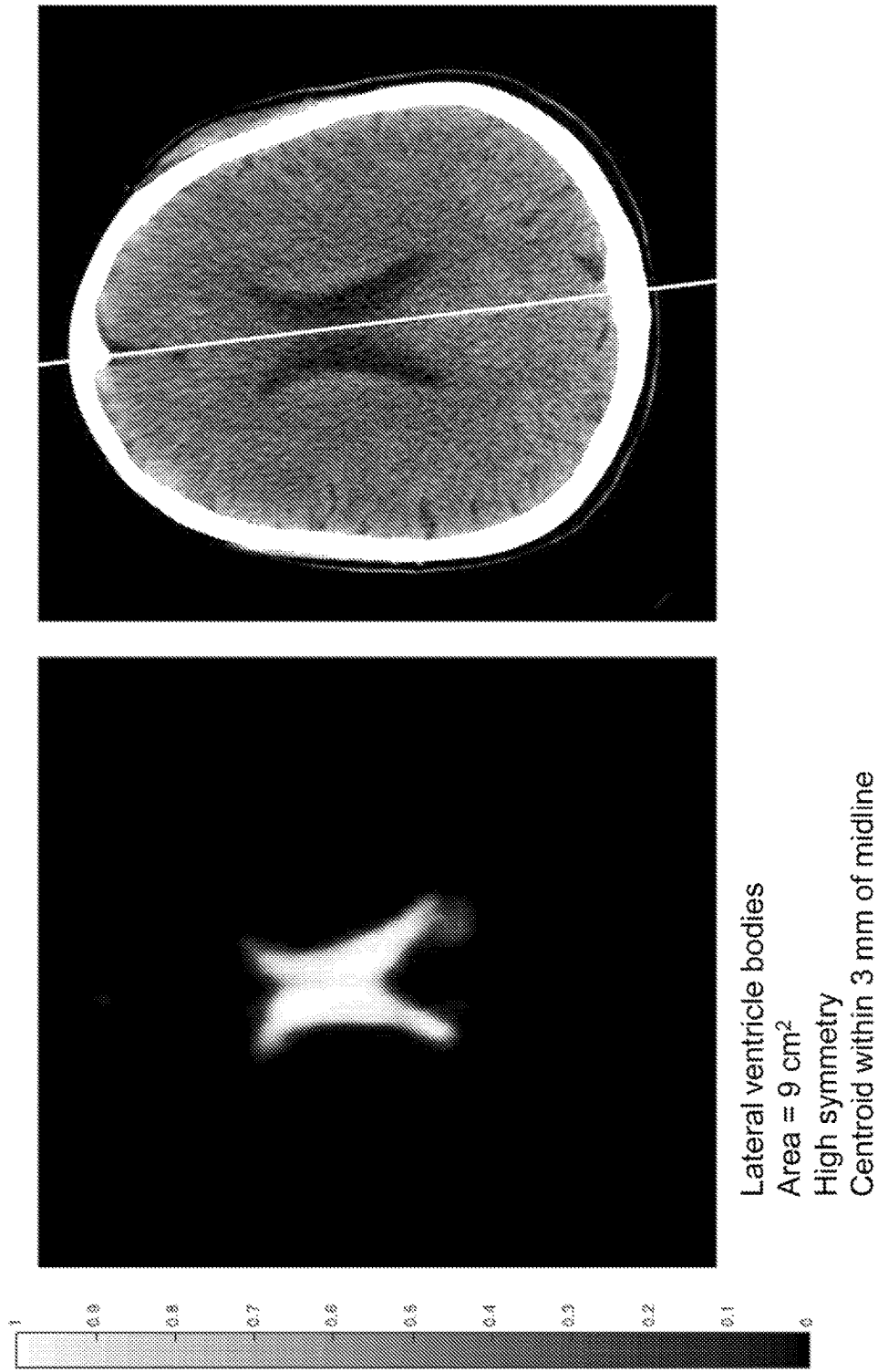
FIG. 17 shows an example application of a system described herein for detection and localization of the ventricular system and assessment of its morphology and size for evidence of intracranial mass effect, including midline shift and hydrocephalus, using a fully convolutional neural network.

Rapid detection, mapping and measurement of the lateral ventricular area using an FCNN trained with dense pixel labeling (FIG. 17).

The original head CT image is on the right side of FIG. 17 with the midline demarcated with a straight white line. The postprocessed image is on the left side of the figure. The left and right lateral ventricles are demarcated in fully automated fashion using an FCNN after the FCNN has been trained with dense pixelwise labeling from manual segmentations. The FCNN demarcation of the ventricular system relies on the likelihood values that are the output of the FCNN, as shown on the scale bar at the left of the Figure, and does not require the knowledge of CT densities in the image in Hounsfield units. The area of the lateral ventricles in this image is computed by summing the area of the pixels of the image included in the demarcation of the lateral ventricles and is given in square centimeters. Determination of the centroid of the lateral ventricular demarcation by the FCNN, shown to be within 1 mm of midline in this example, represents a fully automated method of quantifying the severity of midline shift.

All references cited herein are incorporated by reference in their entireties.

The foregoing description is intended to illustrate various aspects of the instant technology. It is not intended that the examples presented herein limit the scope of the appended claims. The invention now being fully described, it will be apparent to one of ordinary skill in the art that many changes and modifications can be made thereto without departing from the spirit or scope of the appended claims.

What is claimed:

1. A computer-based method for-evaluation of a head computed tomography (CT) image, the method comprising:
analyzing at least one image from a set of head CT images by identifying, localizing, and quantifying one or more abnormalities including at least one of: intracranial hemorrhage, intracranial mass effect, brain herniation, and hydrocephalus based, at least in part, on a deep learning model, wherein localizing the one or more abnormalities comprises demarcating one or more regions within at least an image of the set of head CT images and wherein quantifying the one or more abnormalities comprises calculating a size of the one or more abnormalities in accordance with the one or more demarcated regions.

2. The method of claim 1, wherein the deep learning model is used for identification, localization and quantification of intracranial hemorrhage, as well as intracranial mass effect including at least one of midline shift, brain herniation, and hydrocephalus.

3. The method of claim 2, wherein the deep learning model includes a convolutional neural network.

4. The method of claim 3, wherein the convolutional neural network is a fully convolutional neural network, and further includes training of the convolutional neural network using pixel-wise labeling from manual segmentation of the head CT image.

5. The method of claim 4, wherein the convolutional neural network includes multi-class pixel-wise labeling for classification of the feature of interest, including classifying an intracranial hemorrhage as intraparenchymal, subarachnoid, subdural or epidural.

6. The method of claim 4, wherein the convolutional neural network is trained on only a subset of the pixel-wise labels to aid in the detection, localization, and quantification of sparse features of the set of head CT images, including small intracranial hemorrhages.

7. The method of claim 3, wherein the convolutional neural network includes convolutional kernels that employ dilated receptive fields.

8. The method of claim 3, wherein the convolutional neural network employs deep residual learning.

9. The method of claim 3, wherein the convolutional neural network is a region-based convolutional neural network employing ground truth bounding box labeling with multi-class feature classification and bounding box regression.

10. The method of claim 3, wherein the convolutional neural network incorporates spatial location information.

11. The method of claim 3, wherein ensembles of convolutional neural networks are used, with or without other types of machine learning classifiers.

12. The method of claim 3, wherein fine tuning, also known as transfer learning, is used to accelerate training and improve performance of the convolutional neural network.

13. The method of claim 3, wherein distributed deep learning is employed using multiple GPUs to implement at least one of model parallelism and data parallelism.

14. The method of claim 1, further comprising:
evaluating the head CT image for quantitative features.

15. The method of claim 1, wherein the analyzing comprises determining a quantitative feature comprising a volume of an abnormality.

16. The method of claim 15, wherein the abnormality is an intracranial hemorrhage.

17. The method of claim 1, further comprising:
identifying anatomic features including at least one of the falx cerebri, dorsum sella, basilar cisterns, and globes.

18. The method of claim 17, wherein the identifying is based, at least in part, on a Hough transform.

19. The method of claim 17, wherein the analyzing comprises:
determining cerebral midline shift; and
identifying the falx cerebri by application of an edge detection algorithm followed by a Hough transform.

20. The method of claim 1, further comprising determining an anatomic location of a hemorrhage, wherein the anatomic location of the hemorrhage is determined by automated registration to an atlas.

21. A medical imaging device, configured to analyze an image according to the method of claim 1.

22. A computing apparatus configured to carry out the method of claim 1.

23. A computer readable medium, encoded with instructions for carrying out the method of claim 1.

24. A computer-based method for evaluation of a head computed tomography (CT) image, the method comprising:
accepting a set of computed tomography (CT) images of a patient's head;
removing skull features, scalp, facial bones, and other extracranial soft tissues from the set of images;
analyzing at least one image of the set of CT images by identifying, localizing, and quantifying one or more abnormalities including at least one of: intracranial hemorrhage, intracranial mass effect, midline shift, brain herniation, and hydrocephalus based, at least in part, on a deep learning model, wherein localizing the one or more abnormalities comprises demarcating one or more regions within at least an image of the set of head CT images and wherein quantifying the one or more abnormalities comprises calculating a size of the one or more abnormalities in accordance with the one or more demarcated regions; and
providing information resulting from the analysis to a clinician.

25. The method of claim 24, wherein the removing is performed by:
thresholding at a high Hounsfield unit number;
closing off discontinuities in a representation of the skull;
creating a continuous high density vault that completely encloses a representation of the brain;
performing a fill operation in order to isolate intracranial pixels.

26. The method of claim 24, wherein the analyzing comprises:
calculating a histogram of CT densities for each image in the set of CT images; and
fitting the histograms to a sum of Gaussian distributions centered at approximate locations of the CT densities.

27. The method of claim 24, wherein the analyzing comprises:

demarcating the basilar cisterns and the lateral ventricles to determine brain herniation, hydrocephalus, and midline shift, respectively, using the likelihood values from a trained convolutional neural network.

28. The method of claim 24, wherein the analyzing combines heuristic and deep learning via a convolutional neural network.

* * * * *